(12) United States Patent
Angibaud et al.

(10) Patent No.: US 7,241,777 B2
(45) Date of Patent: Jul. 10, 2007

(54) BENZYLIMIDAZOLYL SUBSTITUTED 2-QUINOLINE AND QUINAZOLINE DERIVATIVES FOR USE AS FARNESYL TRANSFERASE INHIBITORS

(75) Inventors: Patrick René Angibaud, Fontaine-Bellenger (FR); Marc Gaston Venet, Le Mesnil-Esnard (FR); Christophe Meyer, Les Authieux sur le Port Saint Ouen (FR); Henry Joseph Breslin, Lansdale, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 129 days.

(21) Appl. No.: 10/508,185

(22) PCT Filed: Mar. 18, 2003

(86) PCT No.: PCT/EP03/02874

§ 371 (c)(1), (2), (4) Date: Sep. 20, 2004

(87) PCT Pub. No.: WO03/080058

PCT Pub. Date: Oct. 2, 2003

(65) Prior Publication Data

US 2005/0171111 A1  Aug. 4, 2005

(30) Foreign Application Priority Data

Mar. 22, 2002 (EP) .................................. 02076157

(51) Int. Cl.
- A01N 43/42 (2006.01)
- A61K 31/47 (2006.01)
- C07D 215/00 (2006.01)
- A61K 31/498 (2006.01)
- C07D 43/02 (2006.01)

(52) U.S. Cl. ................... 514/312; 546/157; 546/158
(58) Field of Classification Search ........... 514/312, 514/154, 44; 546/157, 158
See application file for complete search history.

(56) References Cited

U.S. PATENT DOCUMENTS 5,968,952 A * 10/1999 Venet et al. ............. 514/312
6,037,350 A * 3/2000 Venet et al. ............. 514/312

FOREIGN PATENT DOCUMENTS

| WO | WO 97/16443 A1 | 5/1997 |
|----|----|----|
| WO | WO 97/21701 A1 | 6/1997 |
| WO | WO 97/36876 A1 | 10/1997 |
| WO | WO 98/40383 A1 | 9/1998 |
| WO | WO 98/49157 A1 | 11/1998 |
| WO | WO 98/55124 A1 | 12/1998 |
| WO | WO 00/01388 A1 | 1/2000 |
| WO | WO 00/01411 A1 | 1/2000 |
| WO | WO 00/12498 A1 | 3/2000 |
| WO | WO 00/12499 A1 | 3/2000 |
| WO | WO 00/39082 A2 | 7/2000 |
| WO | WO 00/47574 A1 | 8/2000 |
| WO | WO 01/53289 A1 | 7/2001 |
| WO | WO 02/24686 A2 | 3/2002 |
| WO | WO 02/24687 A1 | 3/2002 |

OTHER PUBLICATIONS

Kohl et al., "Selective Inhibition of ras-Dependent Transformation by a Farnesyltransferase Inhibitor," Science, 1993, pp. 1934-1937, vol. 260, No. 5116.

Rak et al., "Mutant ras Oncogenes Upregulate VEGF/VPF Expression: Implications for Induction and Inhibition of Tumor Anglogenesis," Cancer Research. 1995, pp. 4575-4580, vol. 55, No. 20.

PCT International Search Report dated Jul. 24, 2003 for PCT Application. No. PCT/EP03/02874 which relates to U.S. Patent Application filed herewith.

* cited by examiner

Primary Examiner—James O. Wilson
Assistant Examiner—Tamthom N. Truong

(57) ABSTRACT

This invention comprises the novel compounds of formula (I)

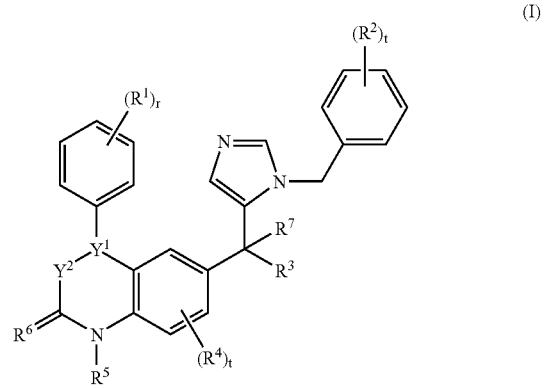

wherein r, t, $Y^1$, $Y^2$, $R^1$, $R^2$, $R^3$, $R^5$, $R^6$ and $R^7$ have defined meanings, having farnesyl transferase inhibiting activity; their preparation, compositions containing them and their use as a medicine.

8 Claims, No Drawings

BENZYLIMIDAZOLYL SUBSTITUTED 2-QUINOLINE AND QUINAZOLINE DERIVATIVES FOR USE AS FARNESYL TRANSFERASE INHIBITORS

CROSS REFERENCE TO RELATED APPLICATIONS

This application is the national stage of Application No. PCT/EP03/02874, filed Mar. 18, 2003 which application claims priority from European Patent No. 02076157.3, filed Mar. 22, 2002.

FIELD OF THE INVENTION

The present invention is concerned with novel (phenyl) methylimidazolyl substituted 2-quinolinone and quinazolinone derivatives, the preparation thereof, pharmaceutical compositions comprising said novel compounds and the use of these compounds as a medicine as well as methods of treatment by administering said compounds.

BACKGROUND OF THE INVENTION

Oncogenes frequently encode protein components of signal transduction pathways, which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes are frequently associated with human cancer. A particular group of oncogenes is known as ras, which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as p21$^{ras}$. Once attached to plasma membranes the mutant or oncogenic forms of p21$^{ras}$ will provide a signal for the transformation and uncontrolled growth of malignant tumor cells. To acquire this transforming potential, the precursor of the p21$^{ras}$ oncoprotein must undergo an enzymatically catalyzed farnesylation of the cysteine residue located in a carboxyl-terminal tetrapeptide. Therefore, inhibitors of the enzymes that catalyze this modification, i.e. farnesyl transferase, will prevent the membrane attachment of p21$^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., *Science* vol 260, 1834–1837, 1993), it has been suggested that farnesyl tranferase inhibitors can be very useful against these types of cancer.

DETAILED DESCRIPTION OF THE INVENTION

In WO 97/16443 WO 97/21701 WO 98/40383 and WO 98/49157 there are described 2-quinoline derivatives, which exhibit farnesyl transferase inhibiting activity. WO 00/39082 describes a class of novel 1,2-annelated quinoline compounds, bearing a nitrogen- or carbon-linked imidazole, which show farnesyl protein transferase and geranylgeranyl transferase inhibiting activity. Other quinolinone compounds having farnesyl transferase inhibiting activity are described in WO 00/12498 WO 00/12499 WO 00/47574 and WO 01/53289.

WO97/36876 describes compounds with farnesyl transferase inhibiting activity. The actual teaching of this publication is limited to compounds of general formula

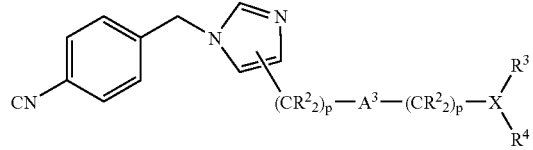

In this application, quinolinone and quinazolinone derivatives are not specifically disclosed.

Unexpectedly, it has been found that the present novel compound, having a phenyl substituent on the 4-position of the quinolinone moiety bearing the (phenyl)methylimidazolyl substituent, show farnesyl protein transferase inhibiting activity. The present compounds can have advantagous properties with regard to solubility and stability.

The present invention concerns compounds of formula (I):

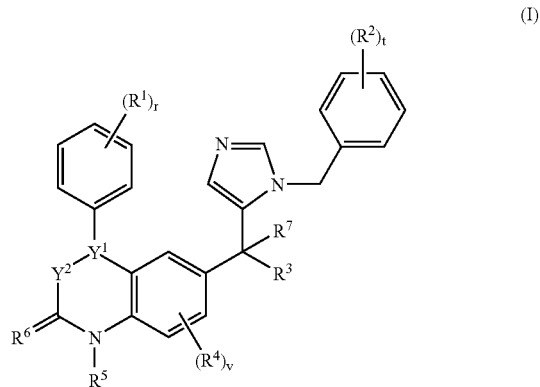

or a pharmaceutically acceptable salt or N-oxide or stereochemically isomeric form thereof, wherein
r is 0, 1, 2, 3;
t is 0, 1 or 2;
v is 0, 1 or 2;
>Y$^1$—Y$^2$— is a trivalent radical of formula $$>C=N— \qquad (y\text{-}1),$$

$$>C=CR^8— \qquad (y\text{-}2),$$

$$>CH—NR^8— \qquad (y\text{-}3), \text{ or}$$

$$>CH—CHR^8— \qquad (y\text{-}4),$$

wherein R$^8$ is hydrogen, halo, cyano, C$_{1-6}$alkyl or hydroxy carbonyl;

R$^1$ is hydrogen, hydroxy, halo, cyano, nitro, C$_{1-6}$alkyl, —(CR$^{16}$R$^{17}$)$_p$—C$_{3-10}$cycloalkyl, cyanoC$_{1-6}$alkyl, hydroxyC$_{1-6}$alkyl, C$_{1-6}$alkyloxyC$_{1-6}$alkyl, —C$_{1-6}$alkyl-NR$^{18}$R$^{19}$, trihalomethyl, C$_{1-6}$alkyloxy, hydroxyC$_{1-6}$alkyloxy, C$_{1-6}$alkyloxyC$_{1-6}$alkyloxy, trihalomethoxy, C$_{2-6}$alkenyl, C$_{2-6}$alkynyl, —CHO, hydroxycarbonyl, $C_{1-6}$alkyloxycarbonyl, —CONR$^{18}$R$^{19}$, mono- or di($C_{1-6}$alkyl)amino$C_{1-6}$alkyloxy, amino$C_{1-6}$alkyloxy, —CR$^{15}$=N—OR$^{16}$;

two R$^1$ substituents adjacent to one another on the phenyl ring may form together a bivalent radical of formula —O—CH$_2$—O— (a-1), —O—CH$_2$—CH$_2$—O— (a-2), —O—CH=CH— (a-3), or —O—CH$_2$—CH$_2$— (a-4), wherein R$^{15}$ and R$^{16}$ are independently hydrogen or $C_{1-6}$alkyl;

R$^{17}$, R$^{18}$ and R$^{19}$ are independently hydrogen, $C_{1-4}$alkyl, hydroxy or $C_{1-4}$alkyloxy;

p is 0 or 1

R$^2$ is hydrogen, halo, cyano, $C_{1-6}$alkyl, hydroxy$C_{1-6}$alkyl, $C_{1-6}$alkyloxy$C_{1-6}$alkyl, trifluoromethyl, hydroxycarbonyl, $C_{1-6}$alkyloxycarbonyl, nitro, cyano$C_{1-6}$alkyl, $C_{2-6}$alkenyl, $C_{2-6}$alkynyl, —CHO, —CR$^{20}$=N—OR$^{21}$;

R$^{20}$ and R$^{21}$ are independently hydrogen or $C_{1-6}$ alkyl;

or two R$^2$ substituents adjacent to one another on the phenyl ring may form together a bivalent radical of formula —O—CH$_2$—O— (a-1), or —O—CH$_2$—CH$_2$—O— (a-2);

R$^3$ is hydrogen, hydroxy, halo, $C_{1-6}$alkyl, halo$C_{1-6}$alkyl, cyano$C_{1-6}$alkyl, amino$C_{1-6}$alkyl, —$C_{1-6}$alkyl-CONR$^{18}$R$^{19}$, mono- or di($C_{1-6}$alkyl)amino$C_{1-6}$alkyl, hydroxy$C_{1-6}$alkyl, $C_{1-6}$alkyloxy$C_{1-6}$alkyl, carbonyl$C_{1-6}$ alkyl, hydroxycarbonyl$C_{1-6}$alkyl, $C_{1-6}$alkyloxycarbonyl$C_{1-6}$alkyl, hydroxycarbonyl, $C_{1-6}$alkyloxycarbonyl or Het$^1$ or a radical of formula —O—R$^9$ (b-1), —NR$^{10}$R$^{11}$ (b-2), or —N=CR$^9$R$^{10}$ (b-3), wherein R$^9$ is hydrogen, $C_{1-6}$alkyl or a radical of formula -Alk-OR$^{12}$ or -Alk-NR$^{13}$R$^{14}$;

R$^{10}$ is hydrogen or $C_{1-2}$alkyl;

R$^{11}$ is hydrogen, hydroxy, $C_{1-6}$alkyl, —(CR$^{16}$R$^{17}$)$_p$—$C_{3-10}$cycloalkyl, $C_{1-6}$alkyloxy, $C_{1-6}$alkylcarbonylamino, $C_{1-6}$alkylcarbonyl, aryl$C_{1-6}$alkylcarbonyl, arylcarbonyl, $C_{1-6}$alkyloxycarbonyl, $C_{1-6}$alkyloxy$C_{1-6}$alkylcarbonyl, aminocarbonyl, aminocarbonylcarbonyl, Het$^1$$C_{1-6}$alkylcarbonyl, $C_{1-6}$alkylaminocarbonyl, mono- or di($C_{1-6}$alkyl)amino$C_{1-6}$alkylcarbonyl, or a radical of formula -Alk-OR$^{12}$ or Alk-NR$^{13}$R$^{14}$;

wherein Alk is $C_{1-6}$alkanediyl;

R$^{12}$ is hydrogen, $C_{1-6}$alkyl, $C_{1-6}$alkylcarbonyl or hydroxy$C_{1-6}$alkyl;

R$^{13}$ is hydrogen, $C_{1-6}$alkyl or $C_{1-6}$alkylcarbonyl;

R$^{14}$ is hydrogen, $C_{1-6}$alkyl or $C_{1-6}$alkylcarbonyl;

R$^4$ is hydrogen, hydroxy, halo, cyano, $C_{1-6}$alkyl or $C_{1-6}$alkyloxy;

R$^5$ is hydrogen, $C_{1-12}$alkyl, —(CR$^{20}$R$^{21}$)$_p$—$C_{3-10}$cycloalkyl, cyano$C_{1-6}$alkyl, —$C_{1-6}$alkylCO$_2$R$^{15}$, aminocarbonyl$C_{1-6}$alkyl-, —$C_{1-6}$alkyl-OR$^{15}$, —$C_{1-6}$alkyl-SR$^{15}$, trifluoromethyl, Ar$^1$$C_{1-6}$alkyl, Het$^1$$C_{1-6}$alkyl, hydroxy$C_{1-6}$alkyl, $C_{1-6}$alkyloxy$C_{1-6}$alkyl, —$C_{1-6}$alkyl-NR$^{20}$R$^{21}$;

R$^6$ is oxygen or R$^5$ and R$^6$ together form a trivalent radical of formula:

—CH=CH—N= (x-1),

—CH=N—N= (x-2), or

—N=N—N= (x-3);

R$^7$ is hydrogen or $C_{1-6}$alkyl or R$^3$ and R$^7$ together with the carbon atom to which they are linked, form a radical of formula C(O);

Ar$^1$ is phenyl or phenyl substituted by one to five substituents each independently selected from halo, hydroxy, amino, cyano, nitro, $C_{1-6}$alkyl, halo$C_{1-6}$alkyl, $C_{1-6}$alkyloxy, OCF$_3$, hydroxycarbonyl, $C_{1-6}$alkyloxycarbonyl, aryloxy, $C_{1-6}$alkylsulfonylamino or phenyl;

Het$^1$ is a mono- or bi-cyclic heterocyclic ring containing one or more heteroatoms selected from oxygen, sulphur and nitrogen and optionally substituted by one or two substituents each independently selected from halo, hydroxy, cyano, nitro, $C_{1-6}$alkyl, halo$C_{1-6}$alkyl, -alkylNR$^{15}$R$^{16}$, $C_{1-6}$alkyloxy, OCF$_3$, hydroxycarbonyl, $C_{1-6}$alkyloxycarbonyl, —CONR$^{15}$R$^{16}$, —NR$^{15}$R$^{16}$, $C_{1-6}$alkylsulfonylamino or phenyl.

As used in the foregoing definitions and hereinafter, halo is generic to fluoro, chloro, bromo and iodo; $C_{1-6}$alkyl defines straight and branched chained saturated hydrocarbon radicals having from 1 to 6 carbon atoms such as, for example, methyl, ethyl, propyl, butyl, pentyl, hexyl 2-methyl-butyl, 2-methylpentyl and the like; $C_{1-12}$ alkyl encompasses the straight and branched chained saturated hydrocarbon radicals as defined in $C_{1-6}$alkyl as well as the higher homologues thereof containing 7 to 12 carbon atoms such as, for example heptyl, octyl, nonyl, decyl, undecyl, dodecyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; halo$C_{1-6}$alkyl defines $C_{1-6}$alkyl containing one or more halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{2-6}$alkynyl defines straight and branched chain hydrocarbon radicals containing one triple bond and having from 2 to 6 carbon atoms such as, for example, ethynyl, 2-propynyl, 3-butynyl, 2-pentynyl, 3-pentynyl, 3-methyl-2-butynyl, and the like; aryl defines phenyl, naphthalenyl, phenyl substituted with one or more substituents each independently selected from halo, $C_{1-6}$alkyl, $C_{1-6}$alkyloxy, trifluoromethyl, cyano, or hydroxycarbonyl; or naphtalenyl substituted with one or more substituents each independently selected from halo, $C_{1-6}$alkyl, $C_{1-6}$alkyloxy, trifluoromethyl, cyano or hydroxycarbonyl; $C_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms that the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms, which said compound might possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:
a) r is 0 or 1;
b) t is 0 or 1;
c) v is 0 or 1;
d) >$Y^1$—$Y^2$— is a trivalent radical of formula (y-1) or (y-2) wherein $R^8$ is hydrogen;
e) $R^1$ is halo, $C_{1-6}$alkyl or $C_{1-6}$alkyloxy;
f) $R^2$ is halo, cyano or two $R^2$ substituents adjacent to one another on the phenyl ring may form together a bivalent radical of formula (a-1);
g) $R^3$ is hydrogen, cyano$C_{1-6}$alkyl, —$C_{1-6}$alkyl-$CONH_2$, $Het^1$ or a radical of formula (b-1) or (b-2) wherein $R^9$ is hydrogen, $R^{10}$ is hydrogen or $C_{1-6}$alkyl and $R^{11}$ is hydrogen, hydroxy or $C_{1-6}$alkyl;
h) $R^4$ is hydrogen;
i) $R^5$ is $C_{1-12}$alkyl;
j) $R^6$ is oxygen or $R^5$ and $R^6$ together form a trivalent radical of formula (x-3);
k) $R^7$ is hydrogen.

Another group of interesting compounds consists of those interesting compounds of formula (I) wherein one or more of the following restrictions apply:
a) r is 1;
b) t is 0 or 1;
c) v is 0;
d) p is 0 or 1;
e) >$Y^1$—$Y^2$— is a trivalent radical of formula (y-2) wherein $R^8$ is hydrogen;
f) $R^1$ is halo;
g) $R^2$ is hydrogen, halo or cyano;
h) $R^3$ is $Het^1$ or a radical of formula (b-1) or (b-2) wherein $R^9$ is hydrogen or $C_{1-6}$alkyl, $R^{10}$ is hydrogen and $R^{11}$ is hydrogen, —$(CH_2)$—$C_{3-10}$cycloalkyl or $C_{1-6}$alkylcarbonyl;
i) $R^4$ is hydrogen;
i) $R^5$ is hydrogen, $C_{1-12}$alkyl, —$(CR^2OR^2)_p$—$C_{3-10}$cycloalkyl or $Ar^1C_{1-6}$alkyl;
k) $R^6$ is oxygen or $R^5$ and $R^6$ together form a trivalent radical of formula (x-3);
l) $R^7$ is hydrogen, $C_{1-6}$alkyl or $R^3$ and $R^7$ together with the carbon atom to which they are linked, form a radical of formula C(O).

A further group of interesting compounds consists of those interesting compounds of formula (I) wherein one or more of the following restrictions apply:
a) $R^1$ is 3-chloro or 3-bromo;
b) $R^2$ is 4-cyano;
c) $R^3$ is hydroxy;
d) $R^5$ is methyl.

A more interesting group of compounds consists of those compounds of formula (I) wherein one or more of the following restrictions apply:
a) r is 1;
b) t is 0 or 1;
c) v is 0;
d) p is 0;
e) >$Y^1$—$Y^2$— is a trivalent radical of formula (y-2) wherein $R^8$ is hydrogen;
f) $R^1$ is halo;
g) $R^2$ is hydrogen or cyano;
h) $R^3$ is a radical of formula (b-1) or (b-2) wherein $R^9$ is hydrogen, $R^{10}$ is hydrogen and $R^{11}$ is hydrogen or $C_{1-6}$alkylcarbonyl;
i) $R^4$ is hydrogen;
i) $R^5$ is $C_{1-12}$alkyl;
k) $R^6$ is oxygen or $R^5$ and $R^6$ together form a trivalent radical of formula (x-3);
l) $R^7$ is hydrogen.

Another group of more interesting compounds are those compounds of formula (I) wherein $R^7$ is hydrogen or $C_{1-6}$alkyl.

Preferred compounds are those compounds of formula (I) wherein r is 1; t is 0 or 1; v is 0; p is 0 or 1; >$Y^1$—$Y^2$— is a trivalent radical of formula (y-2) wherein $R^8$ is hydrogen; $R^1$ is halo; $R^2$ is hydrogen, halo or cyano; $R^3$ is $Het^1$ or a radical of formula (b-1) or (b-2) wherein $R^9$ is hydrogen or $C_{1-6}$alkyl, $R^{10}$ is hydrogen and $R^{11}$ is hydrogen, —$(CH_2)$—$_{3-10}$cycloalkyl or $C_{1-6}$alkylcarbonyl; $R^4$ is hydrogen; $R^5$ is hydrogen, $C_{1-12}$alkyl, —$(CR^{20}R^{21})_p$—$C_{3-10}$cycloalkyl or $Ar^1C_{1-6}$alkyl; $R^6$ is oxygen or $R^5$ and $R^6$ together form a trivalent radical of formula (x-3); $R^7$ is hydrogen, $C_{1-6}$alkyl or R³ and R⁷ together with the carbon atom to which they are linked, form a radical of formula C(O);

More preferred compounds are those compounds of formula (I) wherein r is 1; t is 0 or 1; v is 0; p is 0; >Y¹—Y²— is a trivalent radical of formula (y-2) wherein R⁸ is hydrogen; R¹ is halo; R² is hydrogen or cyano; R³ is a radical of formula (b-1) or (b-2) wherein R⁹ is hydrogen, R¹⁰ is hydrogen and R¹¹ is hydrogen or $C_{1-6}$alkylcarbonyl; R⁴ is hydrogen; R⁵ is $C_{1-12}$alkyl; R⁶ is oxygen or R⁵ and R⁶ together form a trivalent radical of formula (x-3); R⁷ is hydrogen.

Most preferred compound are 4-[[5-[[4-(3-chlorophenyl)-1,2-dihydro-1-methyl-2-oxo-6-quinolinyl]hydroxymethyl]-1H-imidazol-1-yl]methyl]-benzonitrile (compound 3), compound 14 and compound 5.

The compounds of formula (I) and their pharmaceutically acceptable salts and N-oxides and stereochemically isomeric forms thereof may be prepared, for example, by the following processes:

a) Intermediates of formula (II), in which W represents a reactive group and A represents $C_{1-6}$alkyl, preferably methyl, can react with an intermediate of formula (III) to form intermediates of formula (IV). This reaction can be performed in a reaction-inert solvent, such as, for example, tetrahydrofuran in the presence of a strong base, such as, butyl lithium at a temperature ranging from −70° C. to room temperature. Intermediates of formula (IV) can be further hydrolysed under acid conditions with the formation of quinolinones of formula (I) wherein R⁵ is hydrogen and R³ is hydroxy, herein referred to as compounds of formula (I-a).

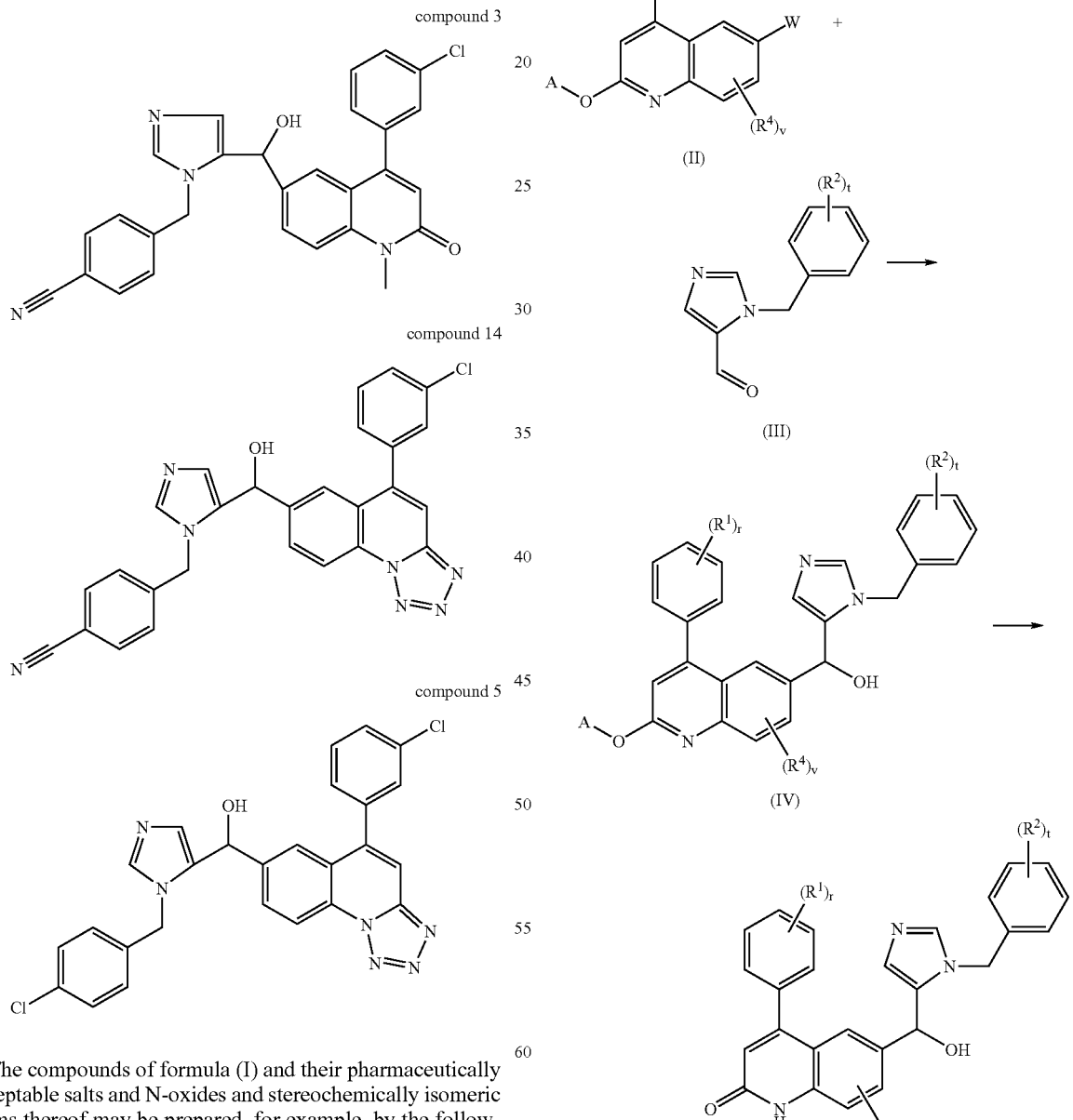

b) Intermediates of formula (V), in which W represents a reactive group can react with an intermediate of formula (III) to form intermediates of formula (VI). This reaction can be performed in a reaction-inert solvent, such as, for example, tetrahydrofuran in the presence of a strong base such as butyl lithium at a temperature ranging from −70° C. to room temperature. Intermediates of formula (VI) can be further converted into quinolinones of formula (I) in which $R^5$ and $R^6$ together form a trivalent radical of formulae (x-3) herein referred to as compounds of formula (I-b-a) and (I-b-b). This reaction can be performed through ring closure with sodiumazide in a reaction inert solvent such as dimethylformamide at a temperature of 90° C.

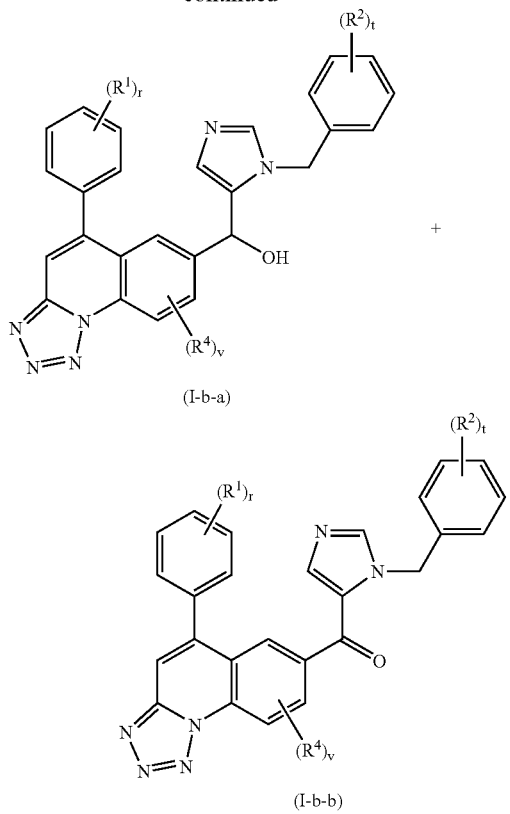

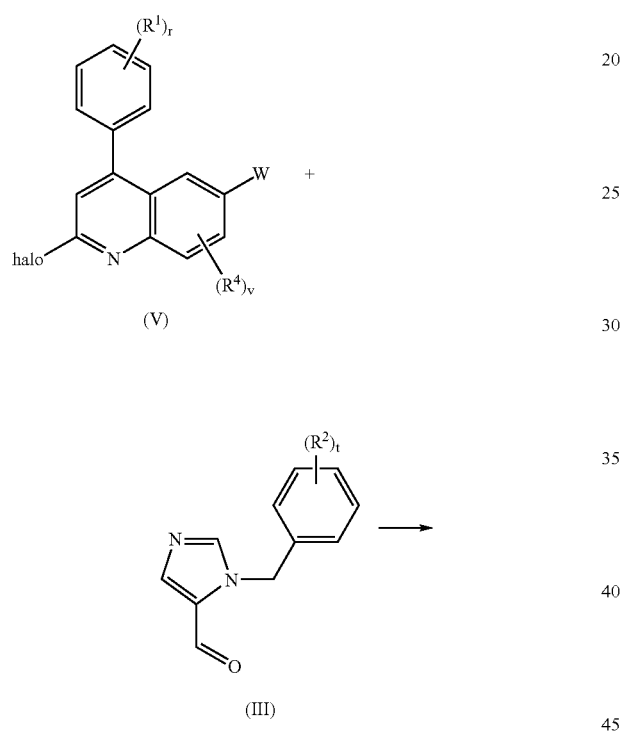

c) Intermediates of formula (VII) can react with an intermediate of formula (III) to form intermediate ketones of formula (IX). This reaction can be performed in a reaction-inert solvent, such as, for example, tetrahydrofuran at a temperature from −70° C. Said reaction requires the presence of a suitable strong base, such as, for example, butyl-lithium in an appropriate silane derivative, such as, for example, triethylchlorosilane. Intermediates of formula (IX) can be further hydrolysed in the presence of a suitable acid, such as HCl. After hydrolysis these intermediates can be further reduced with an appropriate reducing agent such as sodiumborohydride in the. presence of a suitable solvent such as methanol, with the formation of quinazolinones of formula (I) wherein $R^5$ is hydrogen and $R^3$ is hydroxy, herein referred to as compounds of formula (I-c).

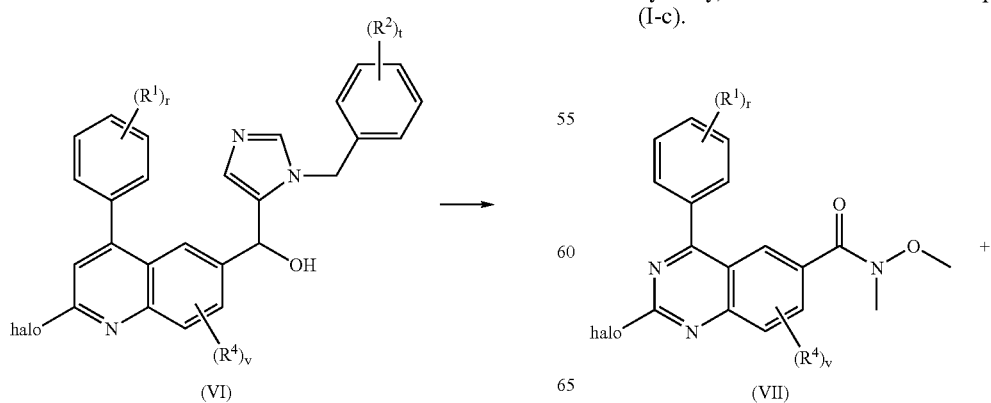

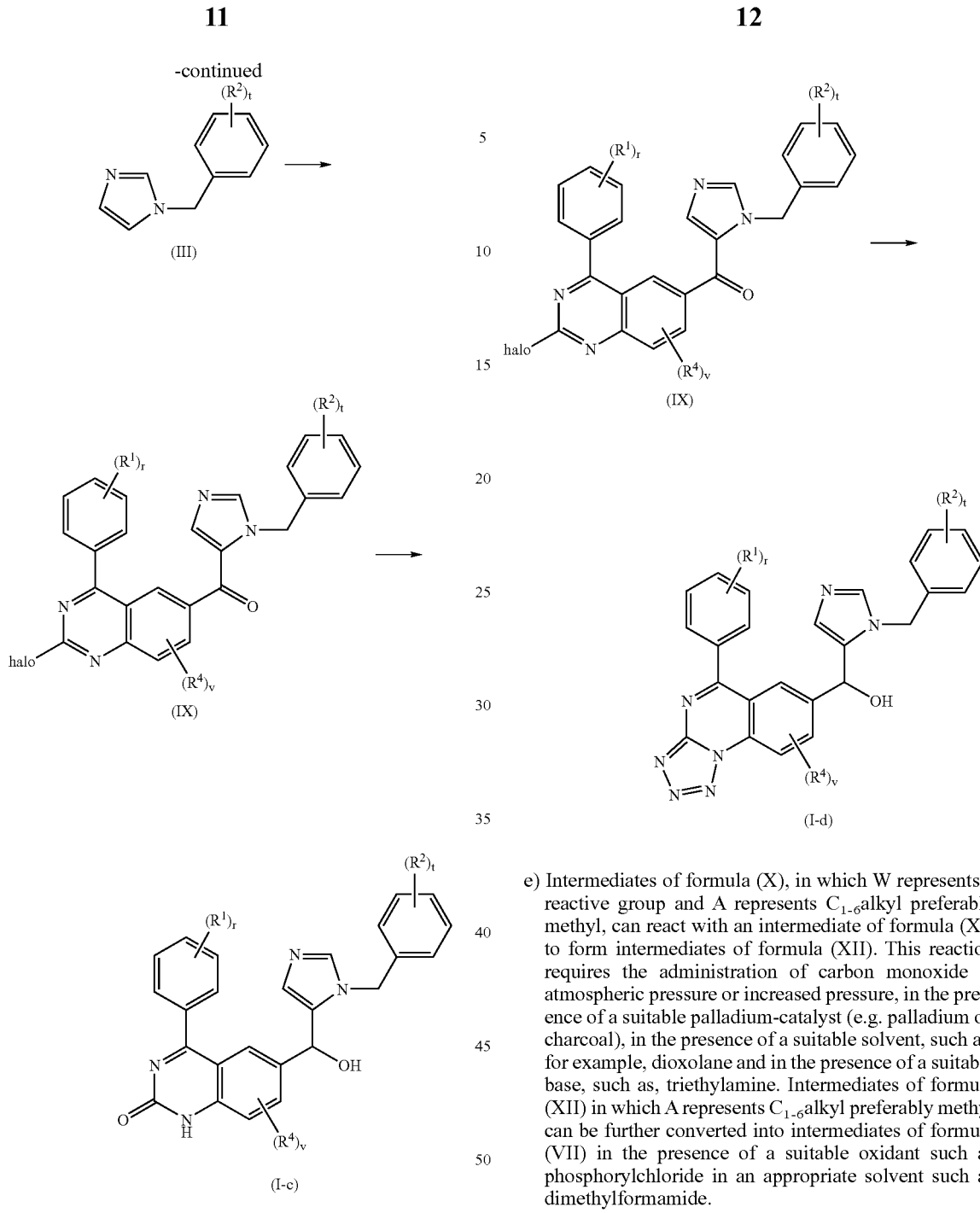

d) Intermediate ketones of formula (IX) can also be reduced with an appropriate reducing agent, such as, sodiumborohydride in the presence of a suitable solvent, such as, methanol. These intermediates can then further be converted into quinazolinones of formula (I) in which $R^5$ and $R^6$ together form a trivalent radical of formula (x-3) herein referred to as compounds of formulae (I-d). This reaction can be performed through ring closure with sodiumazide in a reaction inert solvent, such as, dimethylformamide at a temperature of 90° C.

e) Intermediates of formula (X), in which W represents a reactive group and A represents $C_{1-6}$alkyl preferably methyl, can react with an intermediate of formula (XI) to form intermediates of formula (XII). This reaction requires the administration of carbon monoxide at atmospheric pressure or increased pressure, in the presence of a suitable palladium-catalyst (e.g. palladium on charcoal), in the presence of a suitable solvent, such as, for example, dioxolane and in the presence of a suitable base, such as, triethylamine. Intermediates of formula (XII) in which A represents $C_{1-6}$alkyl preferably methyl can be further converted into intermediates of formula (VII) in the presence of a suitable oxidant such as phosphorylchloride in an appropriate solvent such as dimethylformamide.

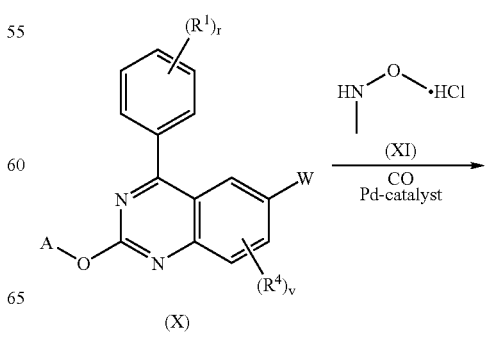

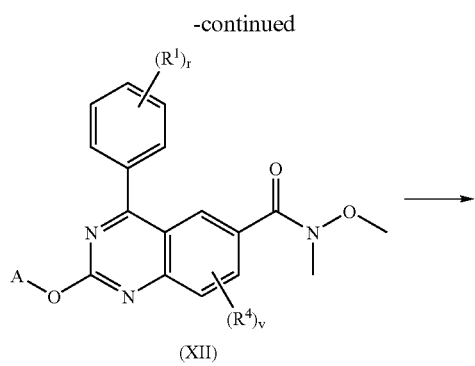

(XII)

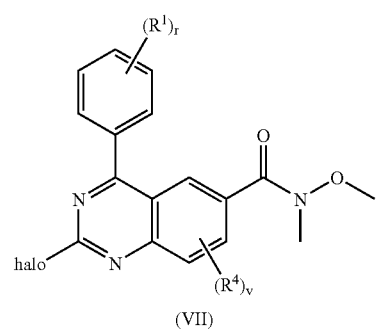

(VII)

f) Intermediated ketones of formula (IX) can be converted into compounds of formula (I-k), defined as a compound of formula (I) wherein $R^3$ is hydroxy and $R^7$ is $C_{1-6}$alkyl by art-known $C_{1-6}$-alkyl addition reactions.

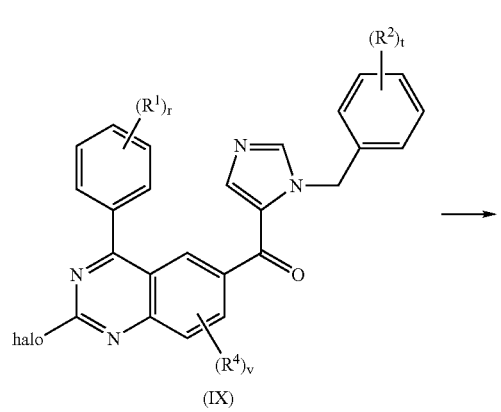

(IX)

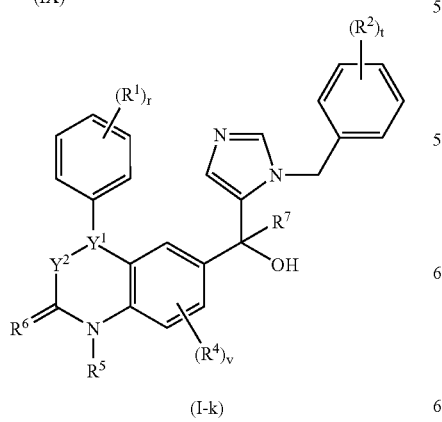

(I-k)

g) Intermediate compounds of formula (VI) can be further converted into intermediate ketones of formula (VIII) in the presence of a reagent such as MnO2 and a suitable solvent such as dioxane. These intermediate ketones of formula (VIII) can be further converted in intermediate ketones of formula (XIII) in which A represents $C_{1-6}$alkyl, preferably methyl. This reaction can be performed in the presence of a suitable solvent such as MeOH in the presence of a suitable reagent such as CH₃ONa/MeOH 30%. Intermediate ketones of formula (XIII) can be further hydrolysed in the presence of a suitable acid, such as HCl to give compounds of formula (I-l).

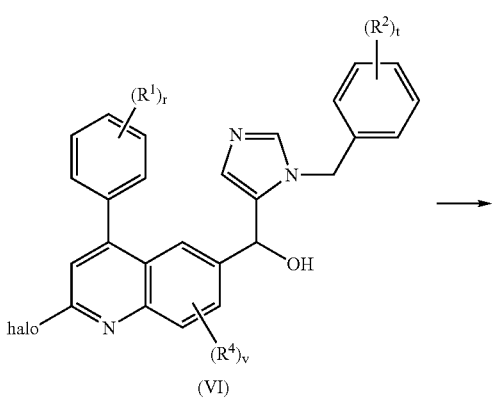

(VI)

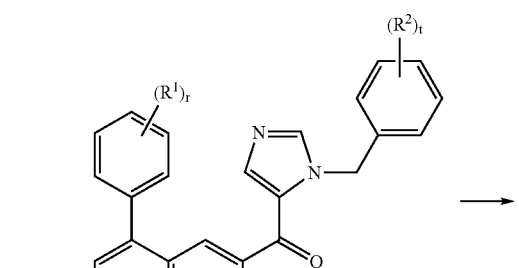

(VIII)

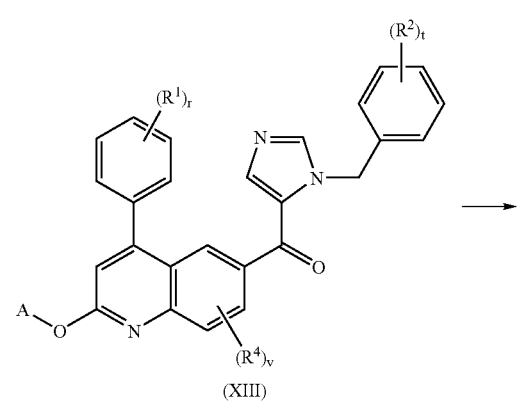

(XIII)

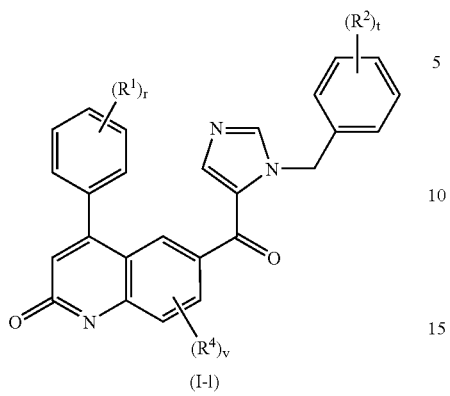

(I-l)

Compounds of formula (I-a), (I-b-a), (I-b-b), (I-c), (I-d), (I-k) and (I-l) can optionally be the subject of one or more of the following conversions in any desired order:

(i) converting a compound of formula (I) into a different compound of formula (I);

(ii) converting a compound of formula (I) into the corresponding acceptable salt or N-oxide thereof;

(iii) converting a pharmaceutically acceptable salt or N-oxide of a compound of formula (I) into the parent compound of formula (I);

(iv) preparing a stereochemical isomeric form of a compound of formula (I) or a pharmaceutically acceptable salt or N-oxide thereof.

Examples of the conversion of one compound of formula (I) into a different compound of formula (I) include the following reactions:

a) Compounds of formula (I-e) wherein $R^3$ is hydroxy and $R^5$ is hydrogen, can be converted into compounds of formula (I-f), defined as a compound of formula (I) wherein $R^3$ is hydroxy and $R^5$ is $C_{1-6}$alkyl by art-known N-alkylation reactions, such as treatment with an alkylhalogenide (e.g. iodomethane) in a reaction inert solvent (e.g. tetrahydrofuran) optionally in the presence of a base, such as, for example sodium hydroxide.

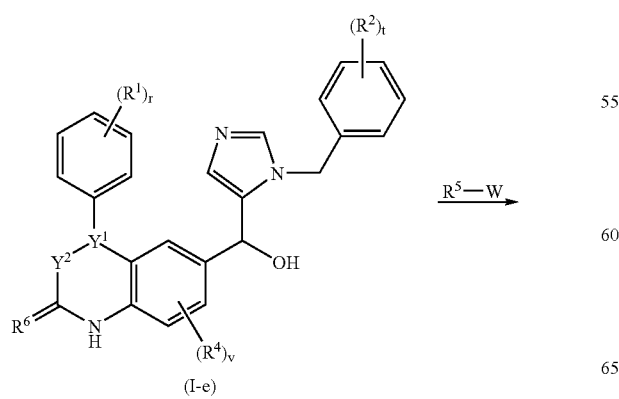

(I-e)

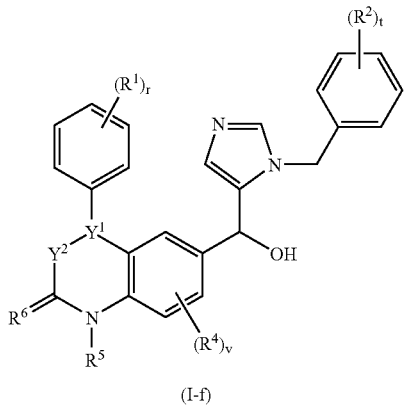

(I-f)

b) Compounds of formula (I-g) wherein $R^3$ is hydroxy, can be converted into compounds of formula (I-h), defined as a compound of formula (I) wherein $R^3$ is hydrogen, by submitting the compounds of formula (I-g) to appropriate reducing conditions, such as, e.g. treatment with sodium borohydride/trifluoroacetic acid.

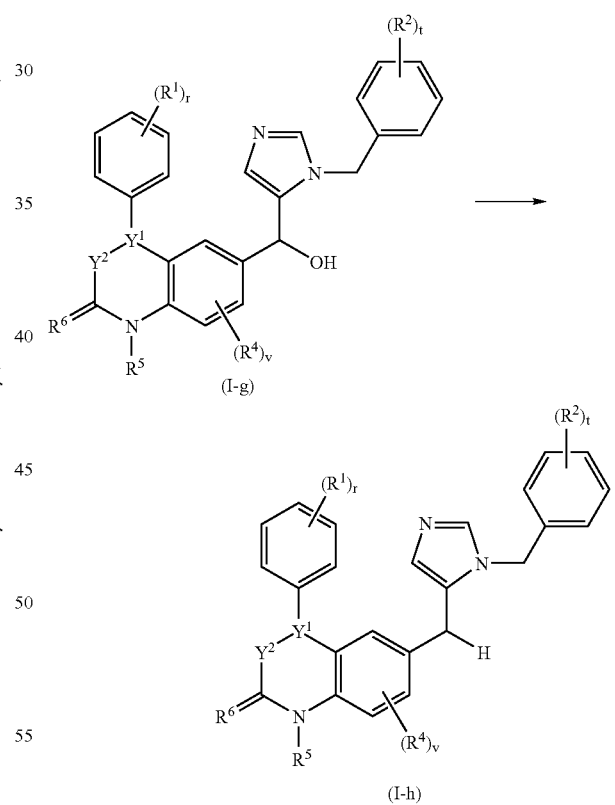

(I-g)

(I-h)

c) Compounds of formula (I-g) can be converted to compounds of formula (I-i) wherein $R^3$ is halo, by reacting the compounds of formula (I-g) with a suitable halogenating agent, such as, e.g. thionyl chloride or phosphorus tribromide. Successively, the compounds of formula (I-i) can be treated with a reagent of formula H—$NR^{10}R^{11}$ in a reaction-inert solvent thereby yielding compounds of formula (I-j).

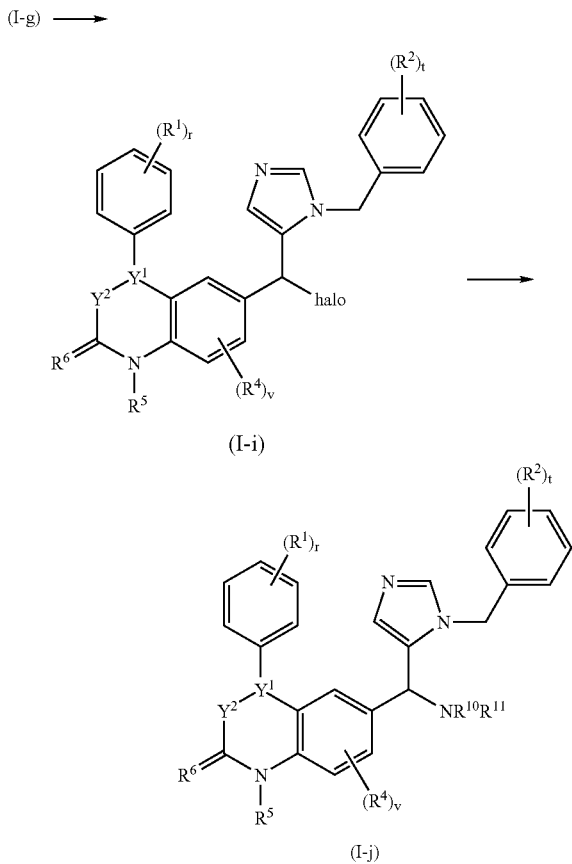

d) Alternatively compounds of formula (I-g) can be converted into compounds of formula (I-j), by treatment with acetic acid ammonium salt at a temperature ranging from 120 to 180° C., or by treatment with sulfamide at a temperature ranging from 120 to 180° C.

e) Compounds of formula (I) in which $>Y^1\text{---}Y^2$ represents a radical of formula (y-1) or (y-2) can be converted into corresponding compounds of formula (I) in which $>Y^1\text{---}Y^2$ represents a radical of formula (y-3) or (y-4) respectively by conventional reduction procedures, for example, hydrogenation or reduction by treatment with sodium borohydride in a suitable solvent, e.g. methanol and vice versa by conventional oxidation procedures such as, for example, treatment with bromine in an appropriate solvent such as, e.g. bromobenzene, or treatment with iodine in the presence of acetic acid and potassium acetate.

f) The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The intermediates and starting materials used in the above-described processes may be prepared in conventional manner using procedures known in the art for example as described in the above-mentioned patent specifications WO 97/16443WO 97/21701WO 98/40383WO 98/49157 and WO 00/39082.

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a potent farnesyl protein transferase (FPTase) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of tumors in vivo by a direct effect on tumor cell growth but also indirectly, i.e. by facilitating tumor-induced angiogenesis (Rak. J. et al, Cancer Research, 55, 4575–4580, 1995). Hence, pharmacologically targeting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma (e.g. advanced breast cancer), kidney carcinoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes. With said inhibition being accomplished by the administration of an effective amount of the compounds described herein, to a subject in need of such a treatment. For example, the benign proliferative disorder neuro-fibromatosis, or tumors in which ras is activated due to mutation or overexpression of tyrosine kinase oncogenes, may be inhibited by the compounds of this invention.

The compound according to the invention can be used for other therapeutic purposes, for example:

a) the sensitisation of tumors to radiotherapy by administering the compound according to the invention before, during or after irradiation of the tumor for treating cancer, for example as described in WO 00/01411;

b) treating athropathies such as rheumatoid arthritis, osteoarhritis, juvenile arthritis, gout, polyarthritis, psoriatic arthritis, ankylosing spondylitis and systemic lupus erythematosus, for example as described in WO 00/01386;

c) inhibiting smooth muscle cell proliferation including vascular proliferative disorders, atherosclerosis and restenosis, for example as described in WO 98/55124;

d) treating inflammatory conditions such as ulcerative colitis, Crohn's disease, allergic rhinilis, graft vs host disease, conjunctivitis, asthma, ARDS, Behcets disease, transplant rejection, uticaria, allergic dermatitis, alopecia areata, scleroderma, exanthem, eczema, dermatomyositis, acne, diabetes, systemic lupus erythematosis, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating pathologies resulting from heterotrimeric G protein membrane fixation including diseases related to following biological functions or disorders; smell, taste, light, perception, neurotransmission, neurodegeneration, endocrine and exocrine gland functioning, autocrine and paracrine regulation, blood pressure, embryogenesis, viral infections, immunological functions, diabetes, obesity;

h) inhibiting viral morphogenesis for example by inhibiting the prenylation or the post-prenylation reactions of a viral protein such as the large delta antigen of hepatitis D virus; and the treatment of HIV infections;

i) treating polycystic kidney disease;

j) suppressing induction of inducible nitric oxide including nitric oxide or cytokine mediated disorders, septic shock, inhibiting apoptosis and inhibiting nitric oxide cytotoxicity;

k) treating malaria.

The compounds of present invention may be particularly useful for the treatment of proliferative diseases, both benign and malignant, wherein the K-ras B isoform is activated as a result of oncogenic mutation.

Hence, the present invention discloses the compounds of formula (I) for use as a medicine as well as the use of these compounds of formula (I) for the manufacture of a medicament for treating one or more of the above mentioned conditions.

For the treatment of the above conditions, the compound of the invention may be advantageously employed in combination with one or more other medicinal agents such as anti-cancer agents for example selected from platinum coordination compounds for example cisplatin or carboplatin, taxane compounds for example paclitaxel or docetaxel, camptothecin compounds for example irinotecan or topotecan, anti-tumor vinca alkaloids for example vinblastine, vincristine or vinorelbine, anti-tumor nucleoside derivatives for example 5-fluorouracil, gemcitabine or capecitabine, nitrogen mustard or nitrosourea alkylating agents for example cyclophosphamide, chlorambucil, carmustine or lomustine, anti-tumor anthracycline derivatives for example daunorubicin, doxorubicin or idarubicin; HER2 antibodies for example trastzumab; and anti-tumor podophyllotoxin derivatives for example etoposide or teniposide; and anti-estrogen agents including estrogen receptor antagonists or selective estrogen receptor modulators preferably tamoxifen, or-alternatively toremifene, droloxifene, faslodex and raloxifene, or aromatase inhibitors such as exemestane, anastrozole, letrazole and vorozole.

For the treatment of cancer the compounds according to the present invention can be administered to a patient as described above, in conjunction with irradiation. Such treatment may be especially beneficial, as farnesyl transferase inhibitors can act as radiosensitisers, for example as described in International Patent Specification WO 00/01411enhancing the therapeutic effect of such irradiation.

Irradiation means ionizing radiation and in particular gamma radiation, especially that emitted by linear accelerators or by radionuclides that are in common use today. The irradiation of the tumor by radionuclides can be external or internal.

Preferably, the administration of the farnesyl transferase inhibitor commences up to one month, in particular up to 10 days or a week, before the irradiation of the tumor. Additionally, it is advantageous to fractionate the irradiation of the tumor and maintain the administration of the farnesyl transferase inhibitor in the interval between the first and the last irradiation session.

The amount of farnesyl protein transferase inhibitor, the dose of irradiation and the intermittence of the irradiation doses will depend on a series of parameters such as the type of tumor, its location, the patient's reaction to chemo- or radiotherapy and ultimately is for the physician and radiologists to determine in each individual case.

The present invention also concerns a method of cancer therapy for a host harboring a tumor comprising the steps of
administering a radiation-sensitizing effective amount of a farnesyl protein transferase inhibitor according to the invention before, during or after
administering radiation to said host in the proximity to the tumor.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate-the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calcuated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.005 mg/kg to 100 mg/kg body weight, and in particular from 0.5 mg/kg to 100 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

The following examples are provided for purposes of illustration.

Hereinafter "THF" means tetrahydrofuran, "EtOAc" means ethyl acetate, and "BuLi" means n-butyl lithium, "DIPE" means diisopropyl ether, "DCM" means dichloromethane, "iPrOH" means isopropyl ether and "MeOH" means methanol.

A. PREPARATION OF THE INTERMEDIATES

EXAMPLE A1 a) Sodium hydroxide (0.62 mol) was dissolved in methanol (100 ml) and the mixture was cooled till room temperature. 1-Bromo-4-nitro-benzene (0.124 mol), followed by 3-chloro-benzeneacetonitrile (0.223 mol) was added dropwise, the temperature rose till 50° C. and the mixture was stirred at room temperature for one night. The mixture was poured into water and ice, the precipitate was filtered off, washed with water and extracted with DCM and methanol. The organic layer was dried ($MgSO_4$), filtered off and evaporated till dryness. The residue was taken up in diethylether, filtered off and dried, yielding 13.2 g (34.8%) of 5-bromo-3-(3-chlorophenyl)-2,1-benzisoxazole, mp. 163° C. (intermediate 1).

b) $TiCl_3$/15% water (1050 ml) was added at room temperature to a solution of intermediate 1 (0.386 mol) in THF (1350 ml) and the mixture was stirred at room temperature for 2 h. The mixture was poured into water and ice and extracted with DCM. The organic layer was decanted, washed with $K_2CO_3$ 10%, dried ($MgSO_4$), filtered off and evaporated, yielding 102 g (85%) of (2-amino-5-bromophenyl)(3-chlorophenyl)-methanone (intermediate 2).

c) A solution of intermediate 2 (0.328 mol) and acetic acid anhydride (0.656 mol) in toluene (1200 ml) was stirred and refluxed for one night. The mixture was evaporated and the product was used without further purification, yielding 139 g (quant.) of N-[4-bromo-2-(3-chlorobenzoyl)phenyl]-acetamide (intermediate 3).

d) 2-Methyl-2-propanol, potassium salt (1.635 mol) was added portionwise at room temperature to a solution of intermediate 3 (0.328 mol) in 1,2-dimethoxyethane (1200 ml) and the mixture was stirred at room temperature for one night. The mixture was evaporated till dryness, the residue was poured into water and ice and decanted. The oily residue was taken up in DIPE, the precipitate was filtered off, washed with EtOAc, acetonitrile and diethyl ether and dried, yielding 88.6 g (80.76%) of 6-bromo-4-(3-chlorophenyl)-2 (1H)-quinolinone (intermediate 4).

e) A mixture of intermediate 4 (0.16 mol) in phosphoryl chloride (500ml) was stirred and refluxed for one night. The mixture was evaporated till dryness, the residue was taken up in ice and water, alkalized with $NH_4OH$ and extracted with DCM. The organic layer was decanted, dried ($MgSO_4$), filtered off and evaporated, yielding 56 g (100%) of 6-bromo-2-chloro-4-(3-chlorophenyl)quinoline, mp.125° C. (intermediate 5).

f) $CH_3ONa$ 30%/methanol (96 ml) was added to a solution of intermediate 5 (0.16 mol) in methanol (500 ml) and the mixture was stirred and refluxed for one night. The mixture was evaporated till dryness. The residue was taken up in DCM, washed with water and decanted. The organic layer was dried ($MgSO_4$), filtered off and evaporated. The residue was taken up in diethylether and DIPE, the precipitate was filtered off and dried, yielding 48 g (86%) of 6-bromo-4-(3-chlorophenyl)-2-methoxyquinoline, mp. 124° C. (intermediate 6).

g) BuLi (0.0226 mol) was added to a solution of intermediate 6 (0.0206 mol) in THF (70 ml), under $N_2$ flow, at −70° C. The mixture was stirred at −70° C. for 15 minutes. A solution of 4-[(5-formyl-1H-imidazol-1-yl)methyl]-benzonitrile (0.0226 mol) in THF (50 ml) was added at −70° C. The mixture was stirred at −70° C. for 1 hour, brought to room temperature and stirred 1 hour at this temperature. The mixture was poured out into ice water, extracted with EtOAc. The organic layer was separated, washed with water, dried (MgSO$_4$), filtered and the solvent was evaporated. The residue was purified by column chromatography over silica gel (15–40 μm) (eluent: DCM/MeOH/NH$_4$OH 97/3/01). The pure fractions were collected and the solvent was evaporated, yielding 0.5 g (5%) of 3-(3-chlorophenyl)-N-[4-[[1-[(4-cyanophenyl)methyl]-1H-imidazol-5-yl]hydroxymethyl]phenyl]-2-propenimidic acid (1E,2E)-methyl ester (intermediate 7).

EXAMPLE A2

Preparation of intermediate 8

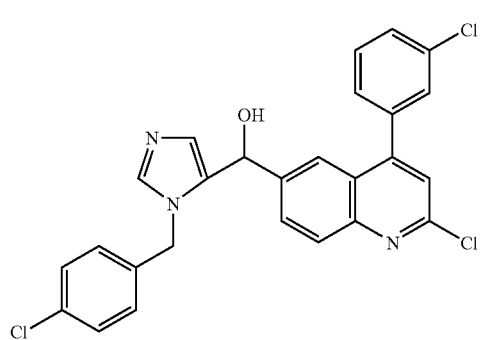

This experiment was performed twice on the same quantities. BuLi 1.6M in hexane (0.0027 mol) was added at –70° C. to a solution of 6-bromo-2-chloro4-(3-chlorophenyl)-quinoline (0.0024 mol) in THF (10 ml) under N$_2$ flow. The mixture was stirred at –70° C. for 1 hour. A solution of 1-[(4-chlorophenyl)methyl]-1H-imidazole-5-carboxaldehyde (0.0026 mol) in THF (7 ml) was added at –70° C. The mixture was stirred at –70° C. for 1 hour, then at room temperature overnight, poured out into ice water and extracted with EtOAc. The organic layer was washed with water, dried (MgSO$_4$), filtered, and the solvent was evaporated. The residue (2.7 g) was purified by column chromatography over silica gel (15–40 μm) (eluent: DCM/MeOH/NH$_4$OH 97/3/0.2 to 95/5/0.1). The pure fractions were collected and the solvent was evaporated, yielding 0.38g (16%) of intermediate 8.

EXAMPLE A3 a) Preparation of intermediate 9

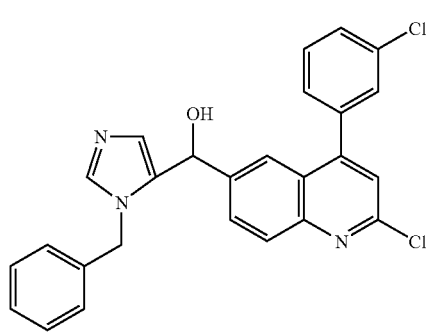

BuLi 1.6M in hexane (0.0167 mol) was added at –78° C. to a solution of 6-bromo-2-chloro4-(3-chlorophenyl)-quinoline (0.0152 mol) in THF (30ml) under N$_2$ flow. The mixture was stirred at –78° C. for 1 hour. A solution of 1-(phenyl-methyl)-1H-imidazole-5-carboxaldehyde (0.0167 mol) in THF (20 ml). was added at –78° C. The mixture was stirred at –78° C. for 1 hour, then at room temperature for 5 hours. Water was added. The mixture was extracted with EtOAc. The organic layer was separated, dried (MgSO$_4$), filtered, and the solvent was evaporated. The residue (7.8 g )was taken up in DCM/MeOH and crystallized from DIPE. The precipitate was filtered off and dried, yielding 0.67 g (9%) of intermediate 9. The filtrate was evaporated. The residue (6.96 g) was purified by column chromatography over silica gel (15–40 μm ) (eluent: DCM/MeOH/NH$_4$OH 95/5/0.2). The pure fractions were collected and the solvent was evaporated, yielding 1.4 g (8%) of intermediate 9.

b) Preparation of intermediate 10

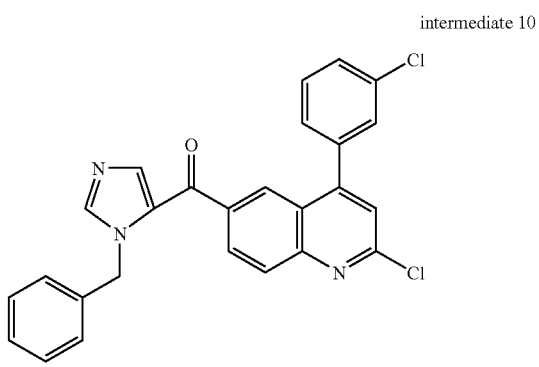

Manganese oxide (0.0014 mol) was added to a mixture of intermediate 9 (0.0014 mol) in dioxane (10 ml). The mixture was stirred and refluxed for 5 hours, then cooled to room temperature, filtered over celite. The filtrate was evaporated, yielding 0.66 g (99%) of intermediate 10, melting point 89° C.

c) Preparation of intermediate 11

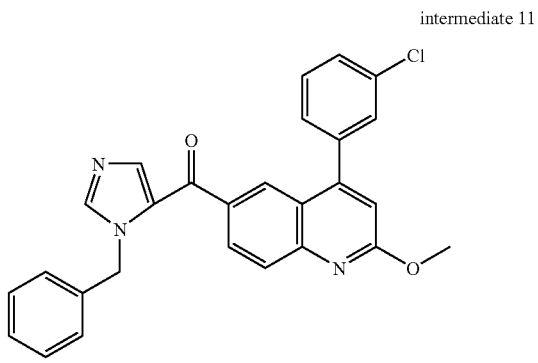

MeOH (10 ml) was added at 5° C. to intermediate 10 (0.0024 mol). MeONa/MeOH 30% (0.0097 mol) was added dropwise at 5° C. The mixture was brought to room temperature, stirred and refluxed for 5 hours, then cooled. The precipitate was filtered off and dried, yielding 0.74 g (67%) of intermediate 11. The filtrate was taken up in DCM, washed with water and extracted with DCM. The organic layer was separated, dried (MgSO$_4$), filtered, and the solvent was evaporated, yielding 0.35 g (31%) of intermediate 11, melting point 143° C.

B. PREPARATION OF THE FINAL COMPOUNDS

EXAMPLE B1

A mixture of intermediate 7 (0.94 mol) in HCl 3N (5 ml) was stirred at reflux overnight, cooled at room temperature and poured out into ice water. DCM and methanol (little quantity) were added. The organic layer was basified by K₂CO₃, separated, dried over MgSO₄, filtered, and the solvent was evaporated, yielding 0.44 g of 4-[[5-[[4-(3-chlorophenyl)-1,2-dihydro-2-oxo-6-quinolinyl]hydroxymethyl]-1H-imidazol-1-yl]methyl]-benzonitrile (compound 1).

EXAMPLE B2

Sodium hydroxide 1N (2 ml), N,N,N-triethylbenzenemethanaminium chloride (0.282 mol) then iodomethane (0.94 mol) were added to a solution of compound 1 (0.94 mol) in THF (2 ml). The mixture was stirred at room temperature overnight, poured out into ice water and extracted with EtOAc. The organic layer was separated, washed with water, dried (MgSO₄), filtered and the solvent was evaporated. The residue was purified by column chromatography over silica gel (15–40 μm) (eluent: DCM/MeOH/NH₄OH 93/7/01). Two fractions were collected and the solvent was evaporated, yielding 0.033 g (7%) of 4-[[5-[[4-(3-chlorophenyl)-1,2-dihydro-1-methyl-2-oxo-6-quinolinyl]methoxymethyl]-1H-imidazol-1-yl]methyl]-benzonitrile (compound 2) and 0.15 g (33%) F2. F2 was crystallized from CH₃CN/diethylether. The precipitate was filtered off and dried, yielding 0.12 g (27%) of 4-[[5-[[4-(3-chlorophenyl)-1,2-dihydro-1-methyl-2-oxo-6-quinolinyl]hydroxymethyl]-1H-imidazol-1-yl]methyl]-benzonitrile (compound 3), melting point 150° C.

EXAMPLE B3

Preparation of

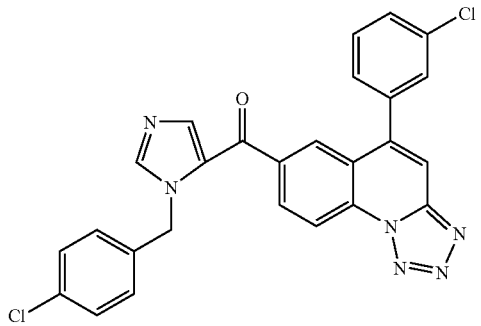

compound 4

EXAMPLE B4

Preparation of compound 5

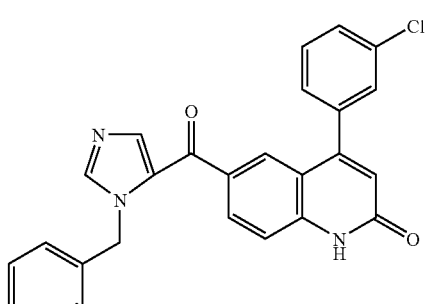

This experiment was performed twice on the same quantities. A mixture of intermediate 8 (0.0002 mol) and sodium azide (0.0005 mol) in DMF (10 ml) was stirred at 140° C. overnight. Water was added. The mixture was extracted with DCM. The organic layer was washed several times with water, dried (MgSO₄), filtered, and the solvent was evaporated. The residues of the two experiments were combined (0.196 g) and were purified by column chromatography over silica gel (10 μm) (eluent: DCM/MeOH 98/2 to 95/5). Two fractions were collected and the solvent was evaporated, yielding 0.043 g F1 and 0.05 g F2. F1 was taken up in DCM. The precipitate was filtered, washed with diethyl ether and dried, yielding 0.041 g (20%) of compound 4, melting point 105° C. F2 was taken up in DCM/MeOH. The precipitate was filtered, washed with diethyl ether and dried, yielding 0.041 g (20%) of compound 5, melting point 140° C.

EXAMPLE B4

Preparation of compound 6

HCl 3N (6 ml) was added to a solution of intermediate 11 (0.0007 mol) in THF (3 ml). The mixture was stirred at 60°

C. for 5 hours, poured out into ice water, basified with NH$_4$OH. The precipitate was filtered off and dried, yielding 0.358 g (>100%) of compound 6.

EXAMPLE B5

Preparation of compound 7

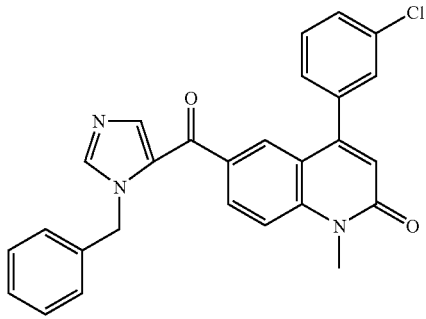

Iodomethane (0.0049 mol) was added to a mixture of compound 6 (0.0024 mol) and benzyltriethylammonium chloride (0.0012 mol) in THF (11 ml) and NaOH 10N (11 ml). The mixture was stirred at room temperature for 6 hours. Water was added. The mixture was extracted with EtOAc. The organic layer was separated, dried (MgSO$_4$), filtered, and the solvent was evaporated. The residue (0.953 g, 84%) was crystallized from DCM/diethyl ether. The precipitate was filtered off and dried, yielding 0.55 g of compound 7, melting point 192° C.

EXAMPLE B6

Preparation of compound 8

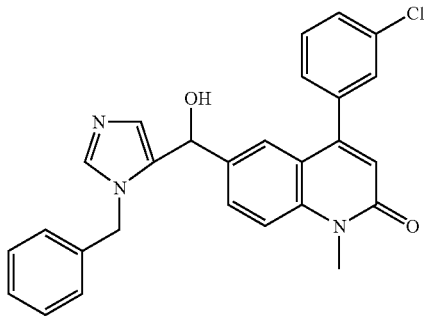

Sodium tetrahydroborate (0.0026 mol) was added at 5° C. to a mixture of compound 7 (0.0012 mol) in THF (3 ml) and MeOH (3 ml) under N$_2$ flow. The mixture was stirred at 5° C. for 2 hours. Ice and water were added. The mixture was extracted with EtOAc. The organic layer was separated, dried (MgSO4), filtered, and the solvent was evaporated, yielding 0.551 g (100%) of compound 8, melting point 188° C.

EXAMPLE B7 a) Preparation of intermediate 12

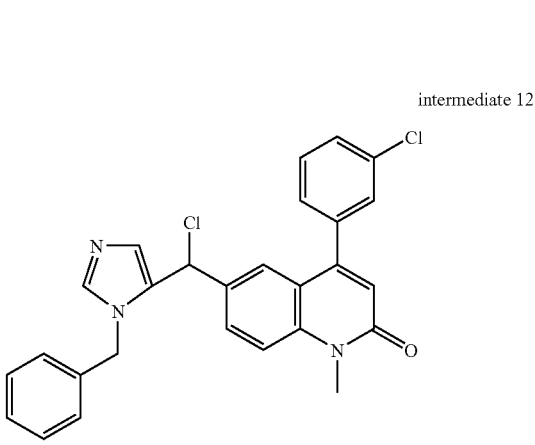

HCl salt

A mixture of compound 8 (0.0001 mol) in thionyl chloride (0.6 ml) was stirred at room temperature for 2 hours. The solvent was evaporated till dryness, yielding 0.065 g of intermediate 12. This product was used directly in the next reaction step.

b) Preparation of compound 9

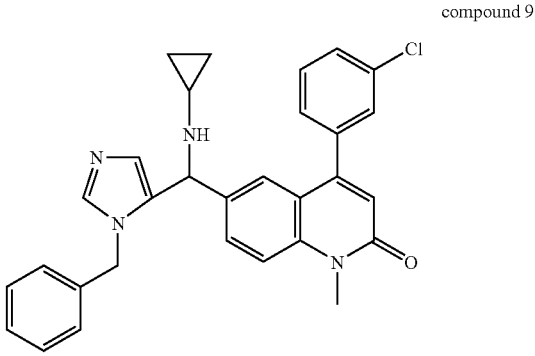

Cyclopropanamine (0.0023 mol) was added to a mixture of intermediate 12 (0.0001 mol) in acetonitrile (2 ml). The mixture was stirred and refluxed for 5 hours. Water was added. The mixture was extracted with DCM. The organic layer was separated, dried (MgSO$_4$), filtered, and the solvent was evaporated. The residue (0.047 g) was purified by column chromatography over silica gel (10 μm) (eluent: DCM/MeOH/NH$_4$OH 98/2/0.1 to 95/5/0.1). The pure fractions were collected and the solvent was evaporated, yielding 0.016 g (25%) of compound 9.

EXAMPLE B8

Preparation of compound 10

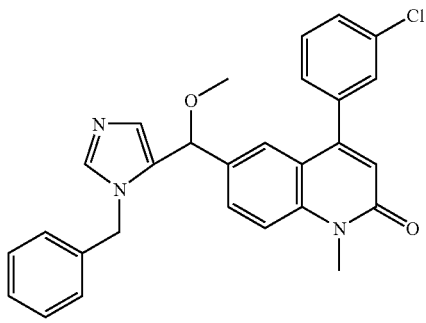

compound 11

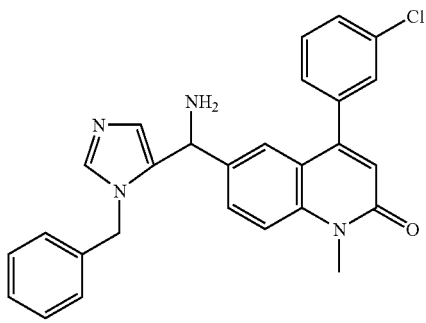

A mixture of intermediate 12 (0.0005 mol) in NH$_3$/MeOH 7N (2.7 ml) was stirred at room temperature for 4 hours, poured out into ice water and extracted with EtOAc. The organic layer was separated, dried (MgSO$_4$), filtered, and the solvent was evaporated. The residue (0.242 g) was purified by column chromatography over silica gel (10 μm) (eluent: DCM/MeOH/NH$_4$OH 96/4/0.1). Two fractions were collected and the solvent was evaporated, yielding 0.042 g F1 and 0.026 g F2. F1 was purified by column chromatography over silica gel (10 μm) (eluent: DCM/MeOH/NH$_4$OH 98/2/0.1). The pure fractions were collected and the solvent was evaporated, yielding 0.016 g (6%) of compound 10. F2 was purified by column chromatography over silica gel (10 μm) (eluent: DCM/MeOH/NH$_4$OH 92/8/0.2). The pure fractions were collected and the solvent was evaporated, yielding 0.01 g (4%) of compound 11.

EXAMPLE B9

Preparation of compound 12

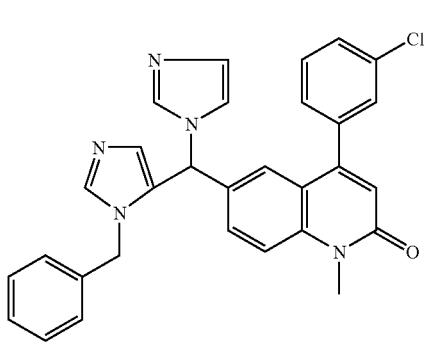

A mixture of compound 8 (0.0001 mol) and 1,1'-carbonyldiimidazole (0.0003 mol) in THF (2 ml) was stirred and refluxed for 24 hours. 1,1'-carbonyldiimidazole (0.0001 mol) was added. The mixture was stirred and refluxed for 2 days, then cooled to room temperature. THF was evaporated. The residue was taken up in DCM. The organic layer was washed with K$_2$CO$_3$ 10%, dried (MgSO$_4$), filtered and the solvent was evaporated. The residue (0.1 g) was purified by column chromatography over silica gel (10 μm) (eluent: toluene/iPrOH/NH$_4$OH 90/10/0.1). The pure fractions were collected and the solvent was evaporated, yielding 0.045 g (56%) of compound 12, melting point 102° C.

EXAMPLE B 10

Preparation of compound 13

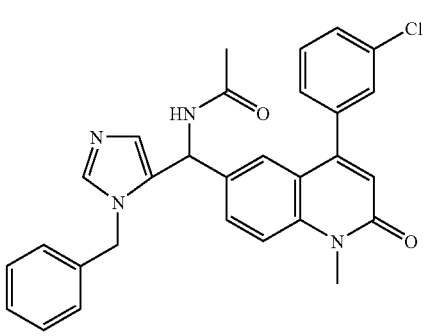

Sulfuric acid concentrated (2 drops) were added to a solution of compound 8 (0.0002 mol) in acetonitrile (1 ml). The mixture was stirred and refluxed for 24 hours. Water was added. The mixture was basified with NH$_4$OH and extracted with DCM. The organic layer was separated, dried (MgSO$_4$), filtered, and the solvent was evaporated. The residue (0.09 g) was purified by column chromatography over silica gel (10 μm) (eluent: toluene/iPrOH/NH$_4$OH 85/15/0.2). The pure fractions were collected and the solvent was evaporated. The residue (0.053 g) was crystallized from DCM/DIPE. The precipitate was filtered off and dried, yielding 0.03 g (38%) of compound 13, melting point 210° C.

TABLE F-1

Table F-1 lists the compounds that were prepared according to one of the above Examples. The following abbreviations were used in the tables: Co.No. stands for Compound Number, Ex. [Xn°] referred to the same method as described in the Xn° example.

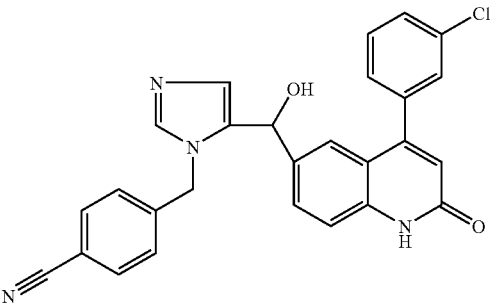

Co. No. 1; Ex. [B1]

TABLE F-1-continued

Table F-1 lists the compounds that were prepared according to one of the above Examples. The following abbreviations were used in the tables: Co.No. stands for Compound Number, Ex. [Xn°] referred to the same method as described in the Xn° example.

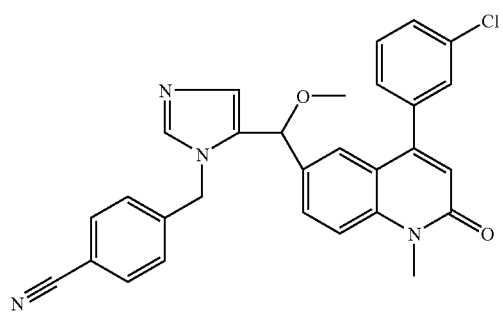

Co. No. 2; Ex. [B2]

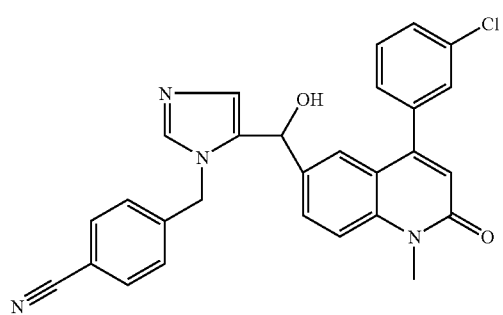

Co. No. 3; Ex. [B2]; mp. 150° C.

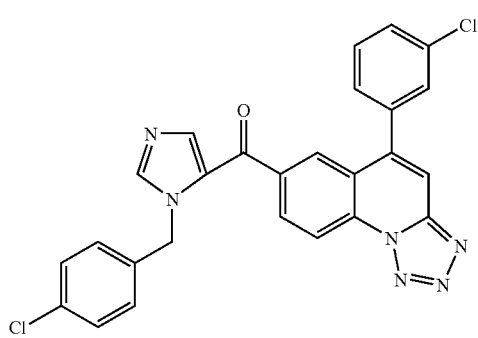

Co. No. 4; Ex. [B3]; mp. 105° C.

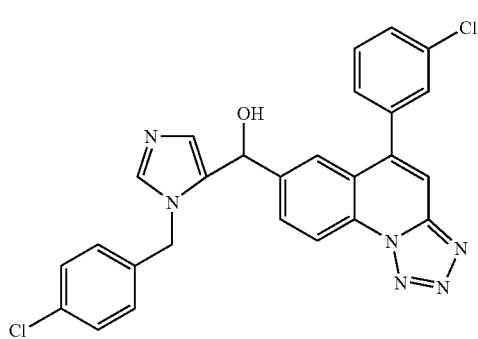

Co. No. 5; Ex. [B3]; mp. 140° C.

TABLE F-1-continued

Table F-1 lists the compounds that were prepared according to one of the above Examples. The following abbreviations were used in the tables: Co.No. stands for Compound Number, Ex. [Xn°] referred to the same method as described in the Xn° example.

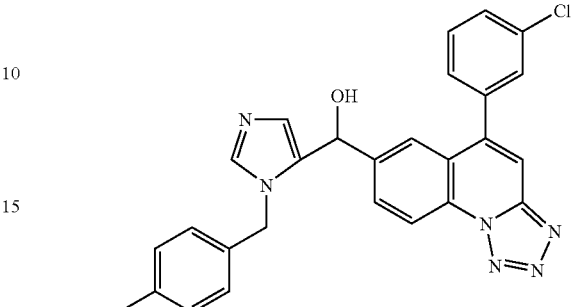

Co. No. 14; Ex. [B3]; mp. 158° C.

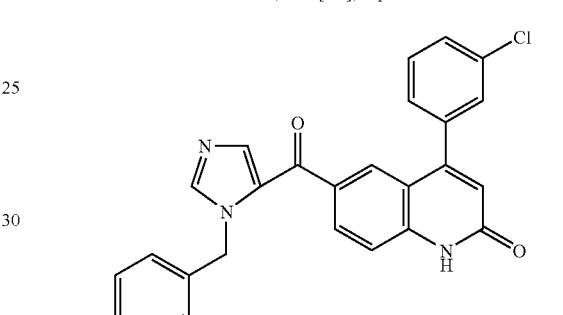

Co. No. 6; Ex. [B4]; MH+ 440, 442 mp. ° C.

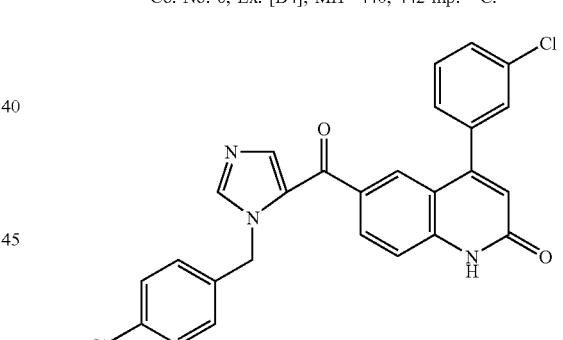

Co. No. 15; Ex. [B4]; mp. 255° C.

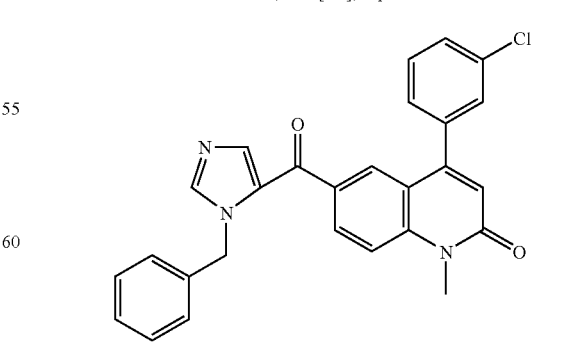

Co. No. 7; Ex. [B5]; mp. 192° C.

TABLE F-1-continued

Table F-1 lists the compounds that were prepared according to one of the above Examples. The following abbreviations were used in the tables: Co.No. stands for Compound Number, Ex. [Xn°] referred to the same method as described in the Xn° example.

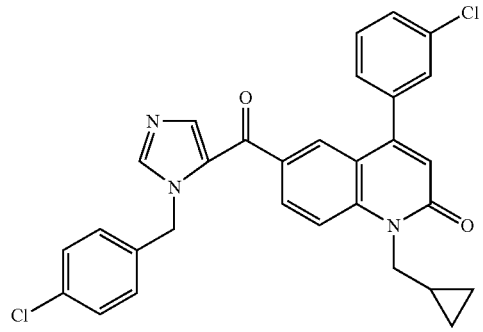

Co. No. 16; Ex. [B5]; mp. 122° C.

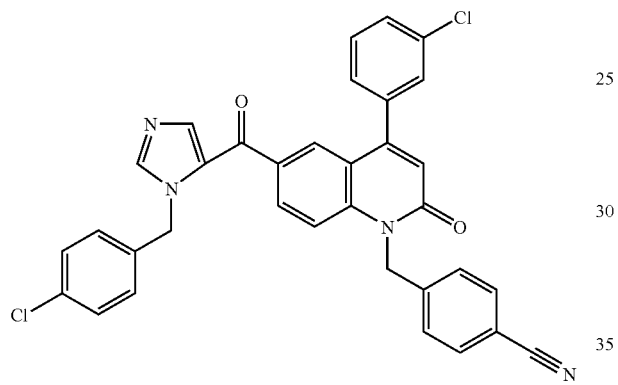

Co. No. 17; Ex. [B5]; mp. 214° C.

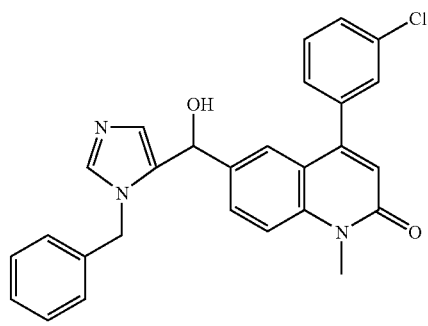

Co. No. 8; Ex. [B6]; mp. 188° C.

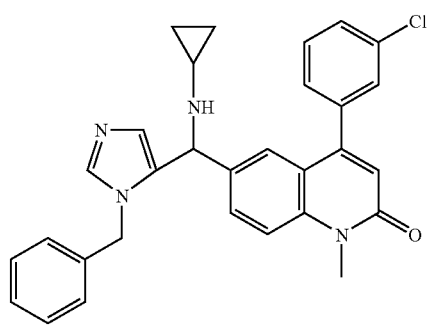

Co. No. 9; Ex. [B7]

TABLE F-1-continued

Table F-1 lists the compounds that were prepared according to one of the above Examples. The following abbreviations were used in the tables: Co.No. stands for Compound Number, Ex. [Xn°] referred to the same method as described in the Xn° example.

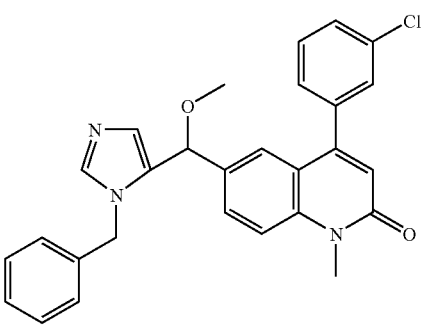

Co. No. 10; Ex. [B8]; MH+ 470, 472 mp. ° C.

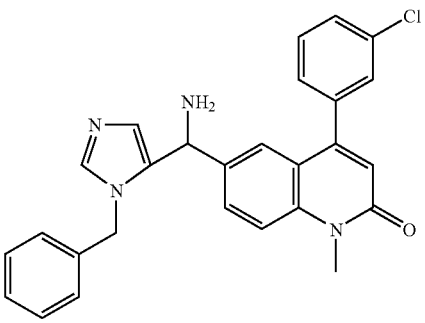

Co. No. 11; Ex. [B8]; MH+ 455, 457

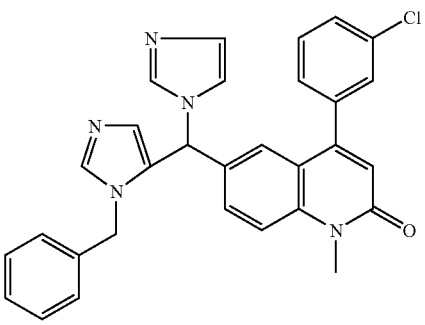

Co. No. 12; Ex. [B9]; mp. 102° C.

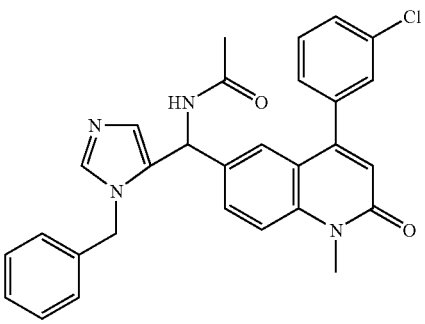

Co. No. 13; Ex. [B10]; mp. 210° C.

C. PHARMACOLOGICAL EXAMPLE

EXAMPLE C.1

"In Vitro Assay for Inhibition of Farnesyl Protein Transferase"

An in vitro assay for inhibition of farnesyl transferase was performed essentially as described in WO 98/40383 pages 33–34. Herein the effects of test compounds are expressed as $pIC_{50}$ (the negative log value of the $IC_{50}$-value) and as % of inhibition at $10^{-7}$ M. 4-[[5-[[4-(3-chlorophenyl)-1,2-dihydro-1-methyl-2-oxo-6-quinolinyl]hydroxymethyl]-1H-imidazol-1-yl]methyl]-benzonitrile (compound 3) has a $pIC_{50}$ of 8.3 and compound 14 has a $pIC_{50}$ of 7.968

EXAMPLE C.2

"Ras-Transformed Cell Phenotype Reversion Assay"

The ras-transformed cell phenotype reversion assay was performed essentially as described in WO 98/40383 pages 34–36.

EXAMPLE C.3

"Farnesyl Protein Transferase Inhibitor Secondary Tumor Model"

The farnesyl protein transferase inhibitor secondary tumor model was used as described in WO 98/40383 page 37.

TABLE F-2

Table F-2 lists the results of the compounds that were tested according to example C.1.

| Co. No. | Enzyme activity pIC50 | % of inhibition at $10^{-7}$ M |
|---|---|---|
| 14 | 7.968 | 87 |
| 5 | <7 | 32 |
| 4 | <7 | 26 |
| 16 | <7 | 18 |
| 17 | <7 | 33 |
| 12 | <7 | 47 |
| 13 | >7 | 65 |
| 9 | <7 | 44 |
| 10 | <7 | 43 |
| 11 | <7 | 49 |
| 3 | 8.264 | 92 |

D. COMPOSITION EXAMPLE

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

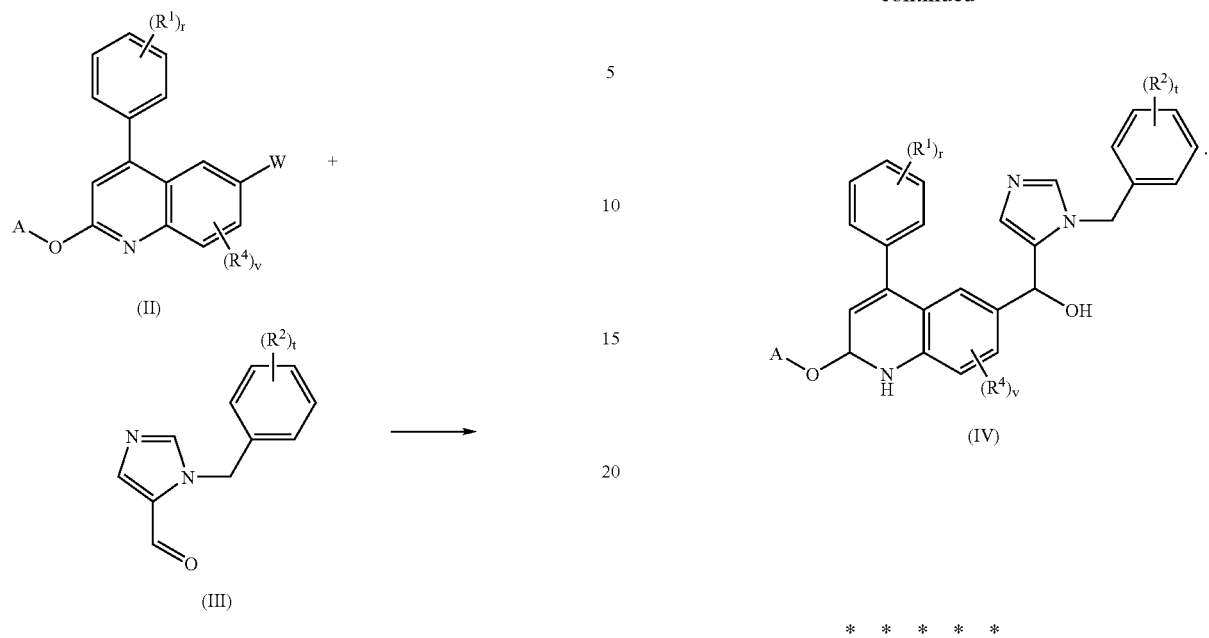

The invention claimed is:
1. A compound of formula (I):

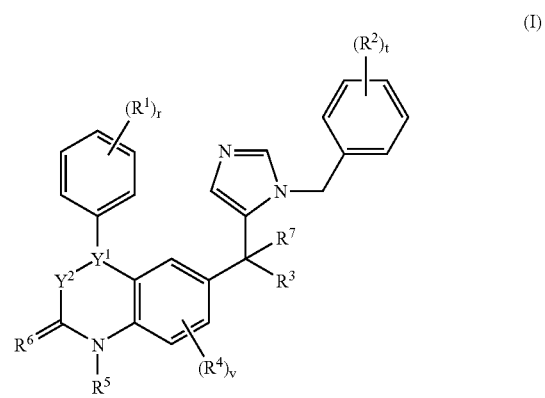

or a pharmaceutically acceptable salt or N-oxide or stereochemically isomeric form thereof, wherein
r is 0, 1, 2, 3;
t is 0, 1 or 2;
v is 0, 1 or 2;
$>Y^1—Y^2—$ is a trivalent radical of formula $$>C=CR^8— \qquad (y-2),$$

$$>CH—CHR^8— \qquad (y-4),$$

wherein $R^8$ is hydrogen, halo, cyano, $C_{1-6}$alkyl or hydroxy carbonyl;
$R^1$ is hydrogen, hydroxy, halo, cyano, nitro, $C_{1-6}$alkyl, —$(CR^{16}R^{17})_p$—$C_{3-10}$cycloalkyl, cyano$C_{1-6}$alkyl, hydroxy$C_{1-6}$alkyl, $C_{1-6}$alkyloxy$C_{1-6}$alkyl, —$C_{1-6}$alkyl-$NR^{18}R^{19}$, trihalomethyl, $C_{1-6}$alkyloxy, hydroxy$C_{1-6}$alkyloxy, $C_{1-6}$alkyloxy$C_{1-6}$alkyloxy, trihalomethoxy, $C_{2-6}$alkenyl, $C_{2-6}$alkynyl, —CHO, hydroxycarbonyl, $C_{1-6}$alkyloxycarbonyl, —$CONR^{18}R^{19}$, mono- or di($C_{1-6}$alkyl)amino$C_{1-6}$alkyloxy, amino$C_{1-6}$alkyloxy, —$CR^{15}=N—OR^{16}$;
wherein $R^{15}$ and $R^{16}$ are independently hydrogen or $C_{1-6}$alkyl;
$R^{17}$, $R^{18}$ and $R^{19}$ are independently hydrogen, $C_{1-4}$alkyl, hydroxy or $C_{1-4}$alkyloxy;
p is 0 or 1;
$R^2$ is hydrogen, halo, cyano, $C_{1-6}$alkyl, hydroxy$C_{1-6}$alkyl, $C_{1-6}$alkyloxy$C_{1-6}$alkyl, trifluoromethyl, hydroxycarbonyl, $C_{1-6}$alkyloxycarbonyl, nitro, cyano$C_{1-6}$alkyl, $C_{2-6}$alkenyl, $C_{2-6}$alkynyl, —CHO, —$CR^{20}=N—OR^{21}$;
$R^{20}$ and $R^{21}$ are independently hydrogen or $C_{1-6}$ alkyl;
$R^3$ is hydrogen, hydroxy, halo, $C_{1-6}$alkyl, halo$C_{1-6}$alkyl, cyano$C_{1-6}$alkyl, amino$C_{1-6}$alkyl, —$C_{1-6}$alkyl-$CONR^{18}R^{19}$, mono- or di($C_{1-6}$alkyl)amino$C_{1-6}$alkyl, hydroxy$C_{1-6}$alkyl, $C_{1-6}$alkyloxy$C_{1-6}$alkyl, carbonyl$C_{1-6}$ alkyl, hydroxycarbonyl$C_{1-6}$alkyl, $C_{1-6}$alkyloxycarbonylC$_{1-6}$alkyl, hydroxycarbonyl, C$_{1-6}$alkyloxycarbonyl or Het$^1$ or a radical of formula —O—R$^9$ (b-1), —NR$^{10}$R$^{11}$ (b-2), or —N=C R$^9$R$^{10}$ (b-3), wherein R$^9$ is hydrogen, C$_{1-6}$alkyl or a radical of formula -Alk-OR$^{12}$ or -Alk-NR$^{13}$R$^{14}$;

R$^{10}$ is hydrogen or C$_{1-12}$alkyl;

R$^{11}$ is hydrogen, hydroxy, C$_{1-6}$alkyl, —(CR$^{16}$R$^{17}$)$_p$—C$_{3-10}$cycloalkyl, C$_{1-6}$alkyloxy, C$_{1-6}$alkylcarbonylamino, C$_{1-6}$alkylcarbonyl, arylC$_{1-6}$alkylcarbonyl, arylcarbonyl, C$_{1-6}$alkyloxycarbonyl, C$_{1-6}$alkyloxyC$_{1-6}$alkylcarbonyl, aminocarbonyl, aminocarbonylcarbonyl, Het$^1$C$_{1-6}$alkylcarbonyl, C$_{1-6}$alkylaminocarbonyl, mono- or di(C$_{1-6}$alkyl)aminoC$_{1-6}$alkylcarbonyl, or a radical of formula -Alk-OR$^{12}$ or Alk-NR$^{13}$R$^{14}$;

wherein Alk is C$_{1-6}$alkanediyl;

R$^{12}$ is hydrogen, C$_{1-6}$alkyl, C$_{1-6}$alkylcarbonyl or hydroxyC$_{1-6}$alkyl;

R$^{13}$ is hydrogen, C$_{1-6}$alkyl or C$_{1-6}$alkylcarbonyl;

R$^{14}$ is hydrogen, C$_{1-6}$alkyl or C$_{1-6}$alkylcarbonyl;

R$^4$ is hydrogen, hydroxy, halo, cyano, C$_{1-6}$alkyl or C$_{1-6}$alkyloxy;

R$^5$ is hydrogen, C$_{1-12}$alkyl, —(CR$^{20}$R$^{21}$)$_p$—C$_{3-10}$cycloalkyl, cyanoC$_{1-6}$alkyl, —C$_{1-6}$alkylCO$_2$R$^{15}$, aminocarbonylC$_{1-6}$alkyl-, —C$_{1-6}$alkyl-OR$^{15}$, —C$_{1-6}$alkyl-SR$^{15}$, trifluoromethyl, Ar$^1$C$_{1-6}$alkyl, Het$^1$C$_{1-6}$alkyl, hydroxyC$_{1-6}$alkyl, C$_{1-6}$alkyloxyC$_{1-6}$alkyl, —C$_{1-6}$alkyl-NR$^{20}$R$^{21}$;

R$^6$ is oxygen;

R$^7$ is hydrogen, C$_{1-6}$alkyl or R$^3$ and R$^7$ together with the carbon atom to which they are linked, form a radical of formula C(O);

Ar$^1$ is phenyl or phenyl substituted by one to five substituents each independently selected from halo, hydroxy, amino, cyano, nitro, C$_{1-6}$alkyl, haloC$_{1-6}$alkyl, C$_{1-6}$alkyloxy, OCF$_3$, hydroxycarbonyl, C$_{1-6}$alkyloxycarbonyl, aryloxy, C$_{1-6}$alkylsulfonylamino or phenyl;

Het$^1$ is a mono- or bi-cyclic heterocyclic ring containing one or more heteroatoms selected from oxygen, sulphur and nitrogen and optionally substituted by one or two substituents each independently selected from halo, hydroxy, cyano, nitro, C$_{1-6}$alkyl, haloC$_{1-6}$alkyl, -alkylNR$^{15}$R$^{16}$ C$_{1-6}$alkyloxy, OCF$_3$, hydroxycarbonyl, C$_{1-6}$alkyloxycarbonyl, —CONR$^{15}$R$^{16}$, —NR$^{15}$R$^{16}$, C$_{1-6}$alkylsulfonylamino or phenyl.

2. A compound according to claim 1 wherein r is 1; t is 0 or 1; v is 0; >Y$^1$—Y$^2$—is a trivalent radical of formula (y-2) wherein R$^8$ is hydrogen; R$^1$ is halo; R$^2$ is hydrogen, halo or cyano; R$^3$ is Het$^1$ or a radical of formula (b-1) or (b-2) wherein R$^9$ is hydrogen or C$_{1-6}$alkyl, R$^{10}$ is hydrogen and R$^{11}$ is hydrogen, —(CH$_2$)—C$_{3-10}$cycloalkyl or C$_{1-6}$alkylcarbonyl; R$^4$ is hydrogen; R$^5$ is hydrogen, C$_{1-12}$alkyl, —(CR$^{20}$R$^{21}$)$_p$—C$_{3-10}$cycloalkyl or Ar$^1$C$_{1-6}$alkyl; R$^6$ is oxygen; R$^7$ is hydrogen, C$_{1-6}$alkyl or R$^3$ and R$^7$ together with the carbon atom to which they are linked, form a radical of formula C(O).

3. A compound according to claim 1 in which r is 1; t is 0 or 1; v is 0; >Y$^1$—Y$^2$— is a trivalent radical of formula (y-2) wherein R$^8$ is hydrogen; R$^1$ is halo; p is 0; R$^2$ is hydrogen or cyano; R$^3$ is a radical of formula (b-1) or (b-2) wherein R$^9$ is hydrogen, R$^{10}$ is hydrogen and R$^{11}$ is hydrogen or C$_{1-6}$alkylcarbonyl; R$^4$ is hydrogen; R$^5$ is C$_{1-12}$alkyl; R$^6$ is oxygen; R$^7$ is hydrogen.

4. A compound as claimed in claim 1 wherein the compound is compound 3,

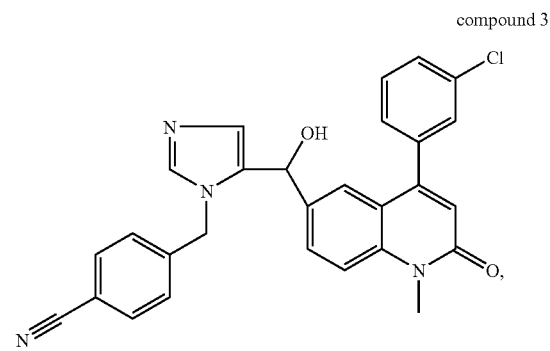

compound 3 or a pharmaceutically acceptable salt thereof.

5. A compound of formula (I-a)

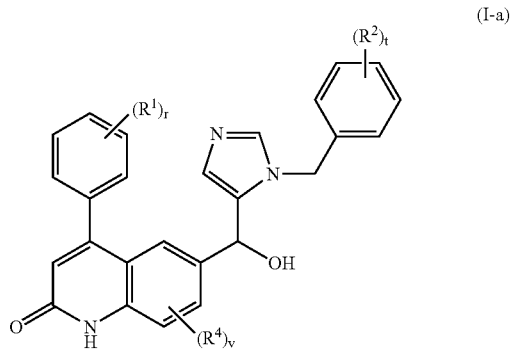

(I-a)

or a pharmaceutically acceptable salt or N-oxide or stereochemically isomeric form thereof, wherein r is 0, 1, 2, 3;

t is 0, 1 or 2;

v is 0, 1 or 2;

R$^1$ is hydrogen, hydroxy, halo, cyano, nitro, C$_{1-6}$alkyl, —(CR$^{16}$R$^{17}$)$_p$—C$_{3-10}$cycloalkyl, cyanoC$_{1-6}$alkyl, hydroxyC$_{1-6}$alkyl, C$_{1-6}$alkyloxyC$_{1-6}$alkyl, —C$_{1-6}$alkyl-NR$^{18}$R$^{19}$, trihalomethyl, C$_{1-6}$alkyloxy, hydroxyC$_{1-6}$alkyloxy, C$_{1-6}$alkyloxyC$_{1-6}$alkyloxy, trihalomethoxy, C$_{2-6}$alkenyl, C$_{2-6}$alkynyl, —CHO, hydroxycarbonyl, C$_{1-6}$alkyloxycarbonyl, —CONR$^{18}$R$^{19}$, mono- or di(C$_{1-6}$alkyl)aminoC$_{1-6}$alkyloxy, aminoC$_{1-6}$alkyloxy, —CR$^{15}$=N—OR$^{16}$;

wherein R$^{15}$ and R$^{16}$ are independently hydrogen or C$_{1-6}$alkyl;

R$^{17}$, R$^{18}$ and R$^{19}$ are independently hydrogen, C$_{1-4}$alkyl, hydroxy or C$_{1-4}$alkyloxy;

p is 0 or 1;

R$^2$ is hydrogen, halo, cyano, C$_{1-6}$alkyl, hydroxyC$_{1-6}$alkyl, C$_{1-6}$alkyloxyC$_{1-6}$alkyl, trifluoromethyl, hydroxycarbonyl, C$_{1-6}$alkyloxycarbonyl, nitro, cyanoC$_{1-6}$alkyl, C$_{2-6}$alkenyl, C$_{2-6}$alkynyl, —CHO, —CR$^{20}$=N—OR$^{21}$;

$R^{20}$ and $R^{21}$ are independently hydrogen or $C_{1-6}$ alkyl;

$R^4$ is hydrogen, hydroxy, halo, cyano, $C_{1-6}$alkyl or $C_{1-6}$alkyloxy.

6. A pharmaceutical composition comprising a pharmaceutically acceptable carrier, and as active ingredient a therapeutically effective amount of a compound as described in claim 1.

7. A process for the preparation of a compound of formula (I-a)

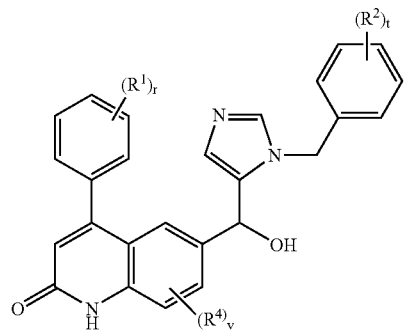

or a pharmaceutically acceptable salt or N-oxide or stereochemically isomeric form thereof, wherein r is 0, 1, 2, 3;
t is 0, 1 or 2;
v is 0, 1 or 2;
$R^1$ is hydrogen, hydroxy, halo, cyano, nitro, $C_{1-6}$alkyl, $-(CR^{16}R^{17})_p-C_{3-10}$cycloalkyl, cyano$C_{1-6}$alkyl, hydroxy$C_{1-6}$alkyl, $C_{1-6}$alkyloxy$C_{1-6}$alkyl, $-C_{1-6}$alkyl-$NR^{18}R^{19}$, trihalomethyl, $C_{1-6}$alkyloxy, hydroxy$C_{1-6}$alkyloxy, $C_{1-6}$alkyloxy$C_{1-6}$alkyloxy, trihalomethoxy, $C_{2-6}$alkenyl, $C_{2-6}$alkynyl, $-$CHO, hydroxycarbonyl, $C_{1-6}$alkyloxycarbonyl, $-$CONR$^{18}$R$^{19}$, mono- or di($C_{1-6}$alkyl)amino$C_{1-6}$alkyloxy, amino$C_{1-6}$alkyloxy, $-$CR$^{15}$=N$-$OR$^{16}$;

wherein $R^{15}$ and $R^{16}$ are independently hydrogen or $C_{1-6}$alkyl;

$R^{17}$, $R^{18}$ and $R^{19}$ are independently hydrogen, $C_{1-4}$alkyl, hydroxy or $C_{1-4}$alkyloxy;

p is 0 or 1;

$R^2$ is hydrogen, halo, cyano, $C_{1-6}$alkyl, hydroxy$C_{1-6}$alkyl, $C_{1-6}$alkyloxy$C_{1-6}$alkyl, trifluoromethyl, hydroxycarbonyl, $C_{1-6}$alkyloxycarbonyl, nitro, cyano$C_{1-6}$alkyl, $C_{2-6}$alkenyl, $C_{2-6}$alkynyl, $-$CHO, $-$CR$^{20}$=N$-$OR$^{21}$;

$R^{20}$ and $R^{21}$ are independently hydrogen or $C_{1-6}$ alkyl;

$R^4$ is hydrogen, hydroxy, halo, cyano, $C_{1-6}$alkyl or $C_{1-6}$alkyloxy.

which comprises the step of hydrolysing an intermediate of formula (IV) wherein the variables have the same definition as defined for the compounds of formula (I-a) and wherein A represents $C_{1-6}$alkyl

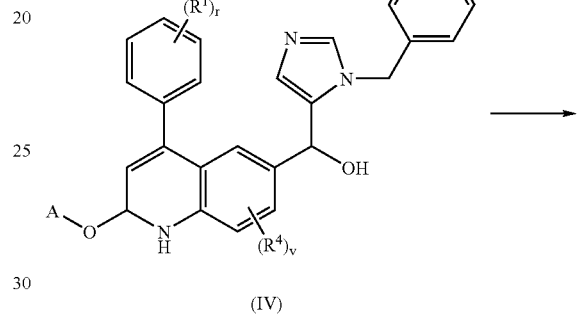

8. A process for the preparation of a compound of formula (I-a) as claimed in claim 7 further comprising the step of reacting an intermediate of formula (II), wherein W represents a reactive group and A represents $C_{1-6}$alkyl is reacted with an intermediate of formula (III) to form intermediate (IV)